US012734202B2

(12) United States Patent
Zhou et al.

(10) Patent No.: US 12,734,202 B2
(45) **Date of Patent: *Sep. 15, 2026**

(54) ONCOLYTIC VIRUS IN COMBINATION WITH IMMUNE CHECKPOINT INHIBITOR FOR TREATING TUMORS

(71) Applicant: JOINT BIOSCIENCES (SH) LTD., Shanghai (CN)

(72) Inventors: Guoqing Zhou, Shanghai (CN); He Yang, Shanghai (CN); Fan Zhang, Shanghai (CN); Suhong Zhang, Shanghai (CN)

(73) Assignee: JOINT BIOSCIENCES (SH) LTD., Shanghai (CN)

( * ) Notice: Subject to any disclaimer, the term of this patent is extended or adjusted under 35 U.S.C. 154(b) by 917 days.

This patent is subject to a terminal disclaimer.

(21) Appl. No.: 18/054,575

(22) Filed: Nov. 11, 2022

(65) Prior Publication Data

US 2023/0190838 A1 Jun. 22, 2023

Related U.S. Application Data

(63) Continuation of application No. PCT/CN2021/093143, filed on May 11, 2021.

(30) Foreign Application Priority Data

May 12, 2020 (CN) ......................... 202010394775.7

(51) Int. Cl.

| | |
|---|---|
| ***A61K 35/766*** | (2015.01) |
| ***A61K 39/00*** | (2006.01) |
| ***A61K 39/395*** | (2006.01) |
| ***A61P 11/00*** | (2006.01) |
| ***A61P 17/00*** | (2006.01) |
| ***A61P 35/00*** | (2006.01) |

(52) U.S. Cl.

CPC ........ *A61K 35/766* (2013.01); *A61K 39/0011* (2013.01); *A61K 39/001188* (2018.08); *A61K 39/3955* (2013.01); *A61P 11/00* (2018.01); *A61P 17/00* (2018.01); *A61P 35/00* (2018.01); *A61K 2039/505* (2013.01); *A61K 2039/5254* (2013.01); *A61K 2039/5256* (2013.01); *A61K 2039/86* (2018.08); *A61K 2039/876* (2018.08); *C12N 2760/20222* (2013.01); *C12N 2760/20232* (2013.01); *C12N 2760/20234* (2013.01); *C12N 2760/20243* (2013.01); *C12N 2760/20262* (2013.01)

(58) Field of Classification Search

None

See application file for complete search history.

(56) References Cited

U.S. PATENT DOCUMENTS

| | | | | |
|---|---|---|---|---|
| 12,496,337 | B2 * | 12/2025 | Zhou | A61K 39/145 |
| 2019/0022203 | A1 * | 1/2019 | Lichty | A61K 39/3955 |

FOREIGN PATENT DOCUMENTS

| | | | | |
|---|---|---|---|---|
| CN | 109069561 A | 12/2018 | | |
| KR | 20190038470 A | 4/2019 | | |
| WO | WO-2019184459 A1 * | 10/2019 | | A61P 35/04 |

OTHER PUBLICATIONS

Gyoung Nyoun Kim, et al., "Creation of Matrix Protein Gene Variants of Two Serotypes of Vesicular Stomatitis Virus as Prime-Boost Vaccine Vectors", Journal of Virology, vol. 89, No. 12, Jun. 15, 2015, pp. 6338-6351.

Weiwei Shen, "Immunovirotherapy with vesicular stomatitis virus and PD-L1 blockade enhances therapeutic outcome in murine acute myeloid leukemia", Blood, vol. 127, No. 11, Mar. 17, 2016, pp. 1449-1458.

Sebastien A. Felt, et al., "Recent advances in vesicular stomatitis virus-based oncolytic virotherapy: a 5-year update", Journal of General Virology, vol. 98, 2017, pp. 2895-2911.

International Search Report Cited in PCT/CN2021/093143, Aug. 13, 2021, 10 Pages.

Written Opinion Cited in PCT/CN2021/093143, Aug. 13, 2021, 6 Pages.

Office Action received in corresponding Korean patent application No. 10-2022-7038519, dated May 21, 2025, 14 pages.

* cited by examiner

*Primary Examiner* — Samira J Jean-Louis
*Assistant Examiner* — Cheng Lu
(74) *Attorney, Agent, or Firm* — Cooper Legal Group, LLC

(57) ABSTRACT

The present application relates to a medicine for treating tumors. A novel attenuated oncolytic virus strain is provided by means of a site-directed mutation of a wild-type virus matrix protein M of a vesicular stomatitis virus. On the basis of the attenuated oncolytic virus strain, an oncolytic virus vaccine is provided by inserting an exogenous gene into the attenuated strain. A medicine capable of treating multiple types of tumors is provided by the use of the oncolytic virus vaccine in combination with the immune checkpoint inhibitor.

8 Claims, 24 Drawing Sheets

Specification includes a Sequence Listing.

SEQUENCE LISTING

```
Sequence total quantity: 13
SEQ ID NO: 1           moltype = DNA  length = 690
FEATURE                Location/Qualifiers
source                 1..690
                       mol_type = genomic DNA
                       note = Indiana strain of vesicular stomatitis virus(VSV
                        MuddSummer)
                       organism = unidentified
SEQUENCE: 1
atgagttcct taaagaagat tctcggtctg aaggggaaag gtaagaaatc taagaaatta  60
gggatcgcac caccccctta tgaagaggac actagcatgg agtatgctcc gagcgctcca  120
attgacaaat cctattttgg agttgacgag atggacacct atgatccgaa tcaattaaga  180
tatgagaaat tcttctttac agtgaaaatg acggttagat ctaatcgtcc gttcagaaca  240
tactcagatg tggcagccgc tgtatcccat tgggatcaca tgtacatcgg aatggcaggg  300
aaacgtccct tctacaaaat cttggctttt ttgggttctt ctaatctaaa ggccactcca  360
gcggtattgg cagatcaagg tcaaccagag tatcacgctc actgcgaagg cagggcttat  420
ttgccacata ggatggggaa gacccctccc atgctcaatg taccagagca cttcagaaga  480
ccattcaata taggtcttta caagggaacg attgagctca caatgaccat ctacgatgat  540
gagtcactgg aagcagctcc tatgatctgg gatcatttca attcttccaa attttctgat  600
ttcagagaga aggccttaat gtttggcctg attgtcgaga aaaaggcatc tggagcgtgg  660
gtcctggact ctatcagcca cttcaaatga                                    690

SEQ ID NO: 2           moltype = AA  length = 229
FEATURE                Location/Qualifiers
source                 1..229
                       mol_type = protein
                       note = Indiana strain of vesicular stomatitis virus(VSV
                        MuddSummer)
                       organism = unidentified
SEQUENCE: 2
MSSLKKILGL KGKGKKSKKL GIAPPPYEED TSMEYAPSAP IDKSYFGVDE MDTYDPNQLR  60
YEKFFFTVKM TVRSNRPFRT YSDVAAAVSH WDHMYIGMAG KRPFYKILAF LGSSNLKATP  120
AVLADQGQPE YHAHCEGRAY LPHRMGKTPP MLNVPEHFRR PFNIGLYKGT IELTMTIYDD  180
ESLEAAPMIW DHFNSSKFSD FREKALMFGL IVEKKASGAW VLDSISHFK              229

SEQ ID NO: 3           moltype = DNA  length = 687
FEATURE                Location/Qualifiers
misc_feature           1..687
                       note = Matrix Protein MM51RL111V221FS226R
source                 1..687
                       mol_type = other DNA
                       organism = synthetic construct
SEQUENCE: 3
atgagttcct taaagaagat tctcggtctg aaggggaaag gtaagaaatc taagaaatta  60
gggatcgcac caccccctta tgaagaggac actagcatgg agtatgctcc gagcgctcca  120
attgacaaat cctattttgg agttgacgag agggacacct atgatccgaa tcaattaaga  180
tatgagaaat tcttctttac agtgaaaatg acggttagat ctaatcgtcc gttcagaaca  240
tactcagatg tggcagccgc tgtatcccat tgggatcaca tgtacatcgg aatggcaggg  300
aaacgtccct tctacaaaat cttggctttt ggttcttcta atctaaaggc cactccagcg  360
gtattggcag atcaaggtca accagagtat cacgctcact gcgaaggcag ggcttatttg  420
ccacatagga tggggaagac ccctcccatg ctcaatgtac cagagcactt cagaagacca  480
ttcaatatag gtctttacaa gggaacgatt gagctcacaa tgaccatcta cgatgatgag  540
tcactggaag cagctcctat gatctgggat catttcaatt cttccaaatt ttctgatttc  600
agagagaagg ccttaatgtt tggcctgatt gtcgagaaaa aggcatctgg agcgtggttc  660
ctggactcta tccggcactt caaatga                                       687

SEQ ID NO: 4           moltype = AA  length = 228
FEATURE                Location/Qualifiers
REGION                 1..228
                       note = Matrix Protein MM51RL111V221FS226RPRT
source                 1..228
                       mol_type = protein
                       organism = synthetic construct
SEQUENCE: 4
MSSLKKILGL KGKGKKSKKL GIAPPPYEED TSMEYAPSAP IDKSYFGVDE RDTYDPNQLR  60
YEKFFFTVKM TVRSNRPFRT YSDVAAAVSH WDHMYIGMAG KRPFYKILAF GSSNLKATPA  120
VLADQGQPEY HAHCEGRAYL PHRMGKTPPM LNVPEHFRRP FNIGLYKGTI ELTMTIYDDE  180
SLEAAPMIWD HFNSSKFSDF REKALMFGLI VEKKASGAWF LDSIRHFK               228

SEQ ID NO: 5           moltype = DNA  length = 20
FEATURE                Location/Qualifiers
misc_feature           1..20
                       note = Primer 1
```

```
source                  1..20
                        mol_type = other DNA
                        organism = synthetic construct
SEQUENCE: 5
aaaaaagtaa cagatatcac                                        20

SEQ ID NO: 6            moltype = DNA  length = 24
FEATURE                 Location/Qualifiers
misc_feature            1..24
                        note = Primer 2
source                  1..24
                        mol_type = other DNA
                        organism = synthetic construct
SEQUENCE: 6
acatttttcc agtttccttt ttgg                                   24

SEQ ID NO: 7            moltype = AA  length = 228
FEATURE                 Location/Qualifiers
REGION                  1..228
                        note = Matrix Protein ML111
source                  1..228
                        mol_type = protein
                        organism = synthetic construct
SEQUENCE: 7
MSSLKKILGL KGKGKKSKKL GIAPPPYEED TSMEYAPSAP IDKSYFGVDE MDTYDPNQLR  60
YEKFFFTVKM TVRSNRPFRT YSDVAAAVSH WDHMYIGMAG KRPFYKILAF GSSNLKATPA  120
VLADQGQPEY HAHCEGRAYL PHRMGKTPPM LNVPEHFRRP FNIGLYKGTI ELTMTIYDDE  180
SLEAAPMIWD HFNSSKFSDF REKALMFGLI VEKKASGAWV LDSISHFK           228

SEQ ID NO: 8            moltype = AA  length = 228
FEATURE                 Location/Qualifiers
REGION                  1..228
                        note = Matrix Protein ML111M51R
source                  1..228
                        mol_type = protein
                        organism = synthetic construct
SEQUENCE: 8
MSSLKKILGL KGKGKKSKKL GIAPPPYEED TSMEYAPSAP IDKSYFGVDE RDTYDPNQLR  60
YEKFFFTVKM TVRSNRPFRT YSDVAAAVSH WDHMYIGMAG KRPFYKILAF GSSNLKATPA  120
VLADQGQPEY HAHCEGRAYL PHRMGKTPPM LNVPEHFRRP FNIGLYKGTI ELTMTIYDDE  180
SLEAAPMIWD HFNSSKFSDF REKALMFGLI VEKKASGAWV LDSISHFK           228

SEQ ID NO: 9            moltype = AA  length = 228
FEATURE                 Location/Qualifiers
REGION                  1..228
                        note = Matrix Protein ML111V221F
source                  1..228
                        mol_type = protein
                        organism = synthetic construct
SEQUENCE: 9
MSSLKKILGL KGKGKKSKKL GIAPPPYEED TSMEYAPSAP IDKSYFGVDE MDTYDPNQLR  60
YEKFFFTVKM TVRSNRPFRT YSDVAAAVSH WDHMYIGMAG KRPFYKILAF GSSNLKATPA  120
VLADQGQPEY HAHCEGRAYL PHRMGKTPPM LNVPEHFRRP FNIGLYKGTI ELTMTIYDDE  180
SLEAAPMIWD HFNSSKFSDF REKALMFGLI VEKKASGAWF LDSISHFK           228

SEQ ID NO: 10           moltype = AA  length = 228
FEATURE                 Location/Qualifiers
REGION                  1..228
                        note = Matrix Protein ML111S226R
source                  1..228
                        mol_type = protein
                        organism = synthetic construct
SEQUENCE: 10
MSSLKKILGL KGKGKKSKKL GIAPPPYEED TSMEYAPSAP IDKSYFGVDE MDTYDPNQLR  60
YEKFFFTVKM TVRSNRPFRT YSDVAAAVSH WDHMYIGMAG KRPFYKILAF GSSNLKATPA  120
VLADQGQPEY HAHCEGRAYL PHRMGKTPPM LNVPEHFRRP FNIGLYKGTI ELTMTIYDDE  180
SLEAAPMIWD HFNSSKFSDF REKALMFGLI VEKKASGAWV LDSIRHFK           228

SEQ ID NO: 11           moltype = AA  length = 228
FEATURE                 Location/Qualifiers
REGION                  1..228
                        note = Matrix Protein ML111V221FS226R
source                  1..228
                        mol_type = protein
                        organism = synthetic construct
SEQUENCE: 11
MSSLKKILGL KGKGKKSKKL GIAPPPYEED TSMEYAPSAP IDKSYFGVDE MDTYDPNQLR  60
YEKFFFTVKM TVRSNRPFRT YSDVAAAVSH WDHMYIGMAG KRPFYKILAF GSSNLKATPA  120
VLADQGQPEY HAHCEGRAYL PHRMGKTPPM LNVPEHFRRP FNIGLYKGTI ELTMTIYDDE  180
```

-continued

```
SLEAAPMIWD HFNSSKFSDF REKALMFGLI VEKKASGAWF LDSIRHFK          228

SEQ ID NO: 12          moltype = AA  length = 120
FEATURE                Location/Qualifiers
REGION                 1..120
                       note = PD-1 antibody VH
source                 1..120
                       mol_type = protein
                       organism = synthetic construct
SEQUENCE: 12
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 13          moltype = AA  length = 112
FEATURE                Location/Qualifiers
REGION                 1..112
                       note = PD-1 antibody VL
source                 1..112
                       mol_type = protein
                       organism = synthetic construct
SEQUENCE: 13
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KR          112
```

ONCOLYTIC VIRUS IN COMBINATION WITH IMMUNE CHECKPOINT INHIBITOR FOR TREATING TUMORS

CROSS-REFERENCE TO RELATED APPLICATIONS

The present application is a continuation application of PCT application No. PCT/CN2021/093143, filed on May 11, 2021, which claims priority to Chinese patent application No. 202010394775.7, filed on May 12, 2020. The entireties of PCT application No. PCT/CN2021/093143 and Chinese patent application No. 202010394775.7 are hereby incorporated by reference herein and made a part of this specification.

REFERENCE TO AN ELECTRONIC SEQUENCE LISTING

The contents of the electronic sequence listing (SequenceListing_2.xml; Size: 19,947 bytes; and Date of Creation: Dec. 19, 2022) is herein incorporated by reference.

TECHNICAL FIELD

The present application relates to a field of bio-medicine, and, particularly, to a pharmaceutical composition for resisting tumors or treating cancers prepared by using an attenuated oncolytic virus strain and an immune checkpoint inhibitor.

BACKGROUND ART

At present, malignant tumors (cancers) have become one of major public health problems that seriously threaten health of the people in China or even throughout the world. Existing methods for treating cancers mainly include surgery, chemotherapy, radiotherapy and molecular targeted therapy, etc., but known methods have no obvious effect on tumor recurrence and metastasis.

Existing research shows that vesicular stomatitis virus (VSV) can be used as a novel tumor vaccine carrier for promoting an immune response, and thus has been used in tumor treatment. VSV is a prototypical non-segmented negative-stranded RNA virus with a genome size of 11 kb encoding 5 kinds of proteins: a nucleocapsid protein (N), a phosphoprotein (P), a matrix protein (M), a glycoprotein (G) and a large polymerase protein (L). Compared with other oncolytic virus carriers currently in development, the VSV has a small genome and is easy to be operated; has a shorter replication time; has an independent cell cycle; is capable of growing rapidly in a wide range of cell lines; has a higher titer, thereby allowing mass production; and, has no transformation risk during cytoplasmic replication in host cells. This oncolytic virus will not be integrated into DNA, and can avoid nervous system inflammation caused by a wild type virus after being attenuated. Thus, the VSV has a great potential in tumor immunotherapy.

However, separate use of the VSV in tumor immunotherapy suffers a poor response rate. Therefore, there are more and more studies on the use of VSV in combination with other treatment methods. It was found in a study of a papilloma mouse model that the use of VSV in combination with a tumor vaccine significantly improved an antitumors effect. Manish R. Patel et al. from University of Minnesota School of Medicine published a study on treating lung cancers by using JAK/STAT inhibitors (Ruxolitinib) in combination with VSV-IFNβ, which indicated that a better oncolytic treatment effect was achieved by using Ruxolitinib in combination with VSV-IFNβ. An oncolytic virus armed with a variety of cytokines was also used in combination with CAR-T cell therapy, which improved an antitumor activity in an xenograft model.

At present, a revolutionary progress has been made for immunotherapy by use of immune checkpoint inhibitors targeting programmed death 1 (PD-1), programmed death ligand 1 (PD-L1) thereof, etc., in the treatment of a tumor. Unfortunately, most of patients are not sensitive to PD-1 or PD-L1 antibody treatment and the conditions in most of sensitive patients are not completely relieved after treatment.

PD-1 or PD-L1 antibody treatment shows the highest anti tumor effect when being used in tumors with high levels of tumor infiltrating lymphocytes (TILs), high mutation burden and increased PD-L1 expression. These responsive tumors are called as “hot tumors” in immunology, and in contrast, unresponsive tumors are called as “cold tumors”. Studies have shown that the “cold tumors” cannot be treated by using PD-1 or PD-L1 antibody, mainly because of the lack of expression and/or presentation of tumor-associated antigens (TAAs), low density of TILs, inhibited infiltration of immune cell subsets (such as neutrophils, macrophages, regulatory T cells, myeloid derived suppressor cells and natural killer cells), and the lack of an expression of immune suppressive substances (such as IL-10, indolamine-2,3-dioxygenase, CD73, PD-L1 and prostaglandin E2). Based on the above studies, converting “cold tumor” into “hot tumor” has become a research hot spot of improving anti PD-1 or PD-L1 antibody treatment. Among others, oncolytic virus is an ideal treatment approach for improving responses of patients and some tumor types to PD-1 or PD-L1 antibody treatment.

In summary, existing researches make it possible to use the VSV in combination with PD-1 or PD-L1 antibody for treating tumors. However, the use of VSV in combination with PD-1 or PD-L1 antibody for tumor immunotherapy still suffers at least the following problems: (1) a direct use of a VSV wild strain or an attenuated strain in combination with PD-1 or PD-L1 antibody does not achieve a cure rate, and shows no significantly improved effect compared with a treatment method using either of them alone; (2) a wild type VSV still has a certain safety risk, for example, it is known to have relatively strong neurotoxicity to rodents at present, and needs to be subjected to a genetic modification for clinical use, so as to further reduce a pathogenic risk and improve a treatment effectiveness; and (3) a random gene modification may result in a poor oncolytic effect, or failing to be successfully packaged, so that a recombinant virus cannot be prepared at all.

Therefore, providing a VSV recombinant virus with good safety and high cure rate and using the same in combination with PD-1 or PD-L1 antibody or other immune checkpoint inhibitors (such as CTLA-4, LAG-3, TIM-3 antibody and etc.) as a drug has an important scientific research value and application significance in a field of tumor immunotherapy.

SUMMARY

In view of this, the present application provides a medicine for treating tumors, specifically, a medicine using an oncolytic virus vaccine in combination with an immune checkpoint inhibitor (such as PD-1, PD-L1, CTLA-4, LAG-3, TIM-3, SIGLEC15 antibody and etc.) for treating tumors.

In this regard, the present application provides the following technical solutions. A medicine for resisting a tumor or treating a cancer includes both an attenuated oncolytic virus strain and an immune checkpoint inhibitor; a preparation method of the attenuated oncolytic virus strains is as follows: engineering a matrix protein M of the oncolytic virus, and a gene sequence of an engineered matrix protein M is shown in SEQ ID NO: 3.

In some embodiments, the attenuated oncolytic virus strain is based on a VSV MuddSummer subtype strain, and is obtained after at least the following site-directed genic mutation: mutating of methionine at position 51 into arginine; knocking out of leucine-encoding bases at position 111; mutating of valine at position 221 into phenylalanine; and, mutating of serine at position 226 into arginine.

In some embodiments, the attenuated oncolytic virus strain is prepared into an oncolytic virus vaccine, and then into a medicine.

In some embodiments, the oncolytic virus vaccine is prepared by inserting an antigen into the attenuated oncolytic virus strain.

In some embodiments, the antigen is a specific tumor antigen.

In some embodiments, the antigen is one selected from a group consisting of: NY-ESO-1, gp33, gp100, TX103, Mucin-1, WT-1, MART-1, MAGE A1, MAGE A3, MAGE A4, MAGE B2, PRAME, SURVIVIN, MART-1, col6A3, tyrosinase, T antigen, SLC45A2, VCX/Y, HPV, alpha fetoprotei, carcinoembryonic antigen, CA 125, Her2, dopachrome tautomerase, BAGE protein, GAGE protein, survivin, tyrosinase, SSX2, cyclin-A1, KIF20A, MUC5AC, Meloe, Lengsin, kallikrein4, IGF2B3 and glypican 3.

In some embodiments, the immune checkpoint inhibitor is one selected from a group consisting of: anti-PD-1 antibody, anti-PD-L1 antibody, anti-CTLA4 antibody, anti-LAG-3 antibody, anti-TIM-3 antibody and anti-SIGLEC15 antibody.

In some embodiments, the immune checkpoint inhibitor is released in a body before the oncolytic virus vaccine.

In some embodiments, the tumor or the cancer is one selected from a group consisting of: head and neck cancer, melanoma, soft tissue sarcoma, breast cancer, esophageal cancer, lung cancer, ovarian cancer, bladder cancer, liver cancer, cervical cancer, neuroblastoma, synovial sarcoma, and round cell liposarcoma.

The present application has the following technical effects. The present application provides the medicine by using the oncolytic virus vaccine in combination with the immune checkpoint inhibitor (such as PD-1, PD-L1, CTLA-4, LAG-3, TIM-3, SIGLEC15 antibody and etc.) for treating tumors, which can effectively treat various kinds of tumors. In a mouse lung cancer model, a cure rate surprisingly reaches 87.5%, and a better treatment effect on large tumors is also achieved.

In a first aspect, the present application provides a pharmaceutical composition including the attenuated oncolytic virus strain and the immune checkpoint inhibitor, in which the attenuated oncolytic virus strain is a VSV MuddSummer subtype strain with a matrix protein M subjected to an engineering, wherein the engineering includes knocking out of leucine-encoding bases at position 111 of an amino acid sequence of the matrix protein M.

In some embodiments, the engineering of the matrix protein M of the attenuated oncolytic virus strain is knocking out of leucine-encoding bases of the amino acid sequence of the matrix protein M.

In some embodiments, the engineering of the matrix protein M of the attenuated oncolytic virus strain further includes mutating of methionine at position 51 of the amino acid sequence of the matrix protein M into arginine.

In some embodiments, the engineering of the matrix protein M of the attenuated oncolytic virus strain is knocking out of leucine-encoding bases of the amino acid sequence of the matrix protein M and mutating of methionine at position 51 of the amino acid sequence of the matrix protein M into arginine.

In some embodiments, the engineering of the matrix protein M of the attenuated oncolytic virus strain further includes mutating of valine at position 221 of the amino acid sequence of the matrix protein M into phenylalanine.

In some embodiments, the engineering of the matrix protein M of the attenuated oncolytic virus strain is knocking out of leucine-encoding bases at position 111 of the amino acid sequence of the matrix protein M and mutating of valine at position 221 of the amino acid sequence of the matrix protein M into phenylalanine.

In some embodiments, the engineering of the matrix protein M of the attenuated oncolytic virus strain further includes mutating of serine at position 226 of the amino acid sequence of the matrix protein M into arginine.

In some embodiments, the engineering of the matrix protein M of the attenuated oncolytic virus strain is knocking out of leucine-encoding bases at position 111 of the amino acid sequence of the matrix protein M and mutating of serine at position 226 of the amino acid sequence of the matrix protein M into arginine.

In some embodiments, the engineering of the matrix protein M of the attenuated oncolytic virus strain is knocking out of leucine-encoding bases at position 111 of the amino acid sequence of the matrix protein M, mutating of valine at position 221 of the amino acid sequence of the matrix protein M into phenylalanine and mutating of serine at position 226 of the amino acid sequence of the matrix protein M into arginine.

In some embodiments, the engineering of the matrix protein M of the attenuated oncolytic virus strain is the mutating of methionine at position 51 of the amino acid sequence of the matrix protein M into arginine, the knocking out of leucine-encoding bases at position 111 of the amino acid sequence of the matrix protein M, the mutating of valine at position 221 of the amino acid sequence of the matrix protein Minto phenylalanine, and the mutating of serine at position 226 of the amino acid sequence of the matrix protein M into arginine.

In some embodiments, the amino acid sequence of the matrix protein M of the attenuated oncolytic virus strain is any one selected from a group consisting of the following amino acid sequences: SEQ ID NO: 4, SEQ ID NO: 7, SEQ ID NO: 8, SEQ ID NO: 9, SEQ ID NO: 10, and SEQ ID NO: 11.

In a second aspect, the present application further provides a pharmaceutical composition including the oncolytic virus vaccine and the immune checkpoint inhibitor. In particular, the oncolytic virus vaccine is prepared by using the attenuated oncolytic virus strain.

In some embodiments, the oncolytic virus vaccine is prepared by inserting the antigen into the attenuated oncolytic virus strain.

In some embodiments, the antigen is a specific tumor antigen.

In some embodiments, the antigen is one selected from a group consisting of: NY-ESO-1, gp33, gp100, TX103, Mucin-1, WT-1, MART-1, MAGE A1, MAGE A3, MAGE A4, MAGE B2, PRAME, SURVIVIN, MART-1, col6A3, tyrosinase, T antigen, SLC45A2, VCX/Y, HPV, alpha fetoprotei, carcinoembryonic antigen, CA 125, Her2, dopachrome tautomerase, BAGE protein, GAGE protein, survivin, tyrosinase, SSX2, cyclin-A1, KIF20A, MUC5AC, Meloe, Lengsin, kallikrein4, IGF2B3 and glypican 3.

In some embodiments, the immune checkpoint inhibitor is one selected from a group consisting of: anti-PD-1 antibody, anti-PD-L1 antibody, anti-CTLA4 antibody, anti-LAG-3 antibody, anti-TIM-3 antibody and anti-SIGLEC15 antibody.

In some embodiments, the immune checkpoint inhibitor is released in the body before the oncolytic virus vaccine.

In some embodiments, the pharmaceutical composition is used for resisting a tumor or treating a cancer.

In some embodiments, the tumor or cancer is one selected from a group consisting of: head and neck cancer, melanoma, soft tissue sarcoma, breast cancer, esophageal cancer, lung cancer, ovarian cancer, bladder cancer, liver cancer, cervical cancer, neuroblastoma, synovial sarcoma, and round cell liposarcoma.

In a third aspect, the present application further provides an use of the pharmaceutical composition described above in preparing a medicine for resisting a tumor or treating a cancer.

Those skilled in the art can easily perceive other aspects and advantages of the present application according to the following detailed description, which only shows and describes exemplary embodiments of the present application. As those skilled in the art will realize, contents of the present application enable those skilled in the art to modify the disclosed exemplary embodiments without departing from a spirit and a scope of inventions related to the present application. Accordingly, the description in drawings and specification of the present application is only illustrative, not restrictive.

BRIEF DESCRIPTION OF DRAWINGS

Specific technical features of inventions related to the present application are shown in claims. Features and advantages of the inventions related to the present application can be better understood by referring to the exemplary embodiments and drawings described in detail below. A brief description of the drawings is as follows.

DETAILED DESCRIPTION

Figure 1A:
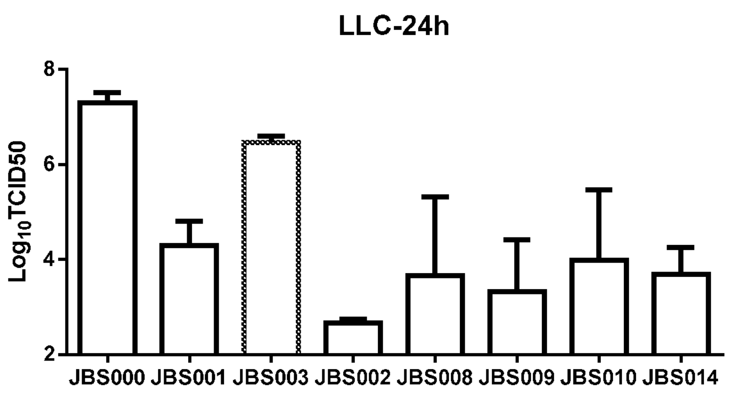
FIGS. 1A-1B are schematic diagrams showing a replication ability of each of attenuated strains in LLC cells and MEF cells in vitro.

Embodiments of inventions related to the present application are illustrated with the following specific examples. Those skilled in the art can easily understand other advantages and effects of inventions related to the present application according to contents disclosed in the specification.

Terms Definition

In the present application, a term “engineered” generally refers to changing a structure and/or a performance of naturally occurring organisms/molecules by an artificial method. A method of engineering can be, for example, modification, mutation, synthetization and/or inserting an exogenous molecule, etc. “Engineered” can be distinguished from natural occurring. For example, if a cell or the organism is operated to change a gene information thereof (for example, introducing a novel genetic material not previously present (such as by transformation, matching, somatic hybridization, transfection, transduction or other mechanisms) or changing or removing a pre-existing genetic material (such as by substitution or deletion mutation)), then they can be considered as “engineered”. For example, the oncolytic virus can be engineered by mutating of a gene encoding an oncolytic viral protein, by inserting of an exogenous gene into an oncolytic viral gene, or by mutating of an amino acid of the oncolytic viral protein.

In the present application, a term “pharmaceutical composition” generally refers to a composition including at least two components, and each component in the pharmaceutical composition can be used in cooperation with each other. In which, “used in cooperation with each other” refers to “used at the same time” or “used respectively”. The components in the pharmaceutical composition can be mixed together or placed in different containers. For example, the pharmaceutical composition includes the attenuated oncolytic virus strain and the immune checkpoint inhibitor described in the present application. The attenuated oncolytic virus strain and the immune checkpoint inhibitor can be administrated at the same time or respectively. The attenuated oncolytic virus strain and the immune checkpoint inhibitor can be mixed together or placed in the different containers respectively.

In the present application, a term “oncolytic virus” generally refers to a virus that can replicate in tumor cells and kill the tumor cells. In certain embodiments, the virus is engineered to improve a selectivity to the tumor cells. In some embodiments, the oncolytic virus is engineered to reduce immunogenicity thereof. In some embodiments, the oncolytic virus is a vesicular stomatitis virus (VSV). In some embodiments, the vesicular stomatitis virus is a vesicular stomatitis virus MuddSummer subtype strain. In some embodiments, a matrix protein M gene of the vesicular stomatitis virus can be subjected to a site-directed mutation.

In the present application, a term “matrix protein M” can be used interchangeably with “M protein”, and generally refers to the matrix protein of the vesicular stomatitis virus. The matrix protein M is an important virulence factor of the VSV, and a protein in the vesicular stomatitis virus known to interfere with an innate immune response of mice. The term “matrix protein M” further includes homologs, orthologs, variants, functional active segments and the like thereof. In the present application, the matrix protein M of wild type vesicular stomatitis virus MuddSummer subtype Indiana strain can include an amino acid sequence shown in SEQ ID NO: 2.

In the present application, a protein mutation site is generally expressed by “amino acid+amino acid site+(amino acid after mutation)”. In the present application, the mutation includes but is not limited to an addition, a substitution, a deletion and/or a knocking out of the amino acid. For example, a term “M51R” generally refers to a mutation of methionine M at position 51 into arginine R. In the present application, a symbol “A” refers to a deletion of the amino acid. For example, a term “ΔL111” generally refers to the deletion of leucine at position 111.

In the present application, a term “antigen” generally refers to an immunogenic proteins. The antigen can be used, for example, to produce an antibody that can bind with the antigen. In some cases, the antigen includes a tumor antigen. In some cases, the antigen includes a melanoma. In some cases, for example, the antigen can be NY-ESO-1.

In the present application, a term “NY-ESO-1” is also called as “New York esophageal squamous cell cancer 1”, which is a cancer-testis antigen (CTA). The NY-ESO-1 described in the present application includes variants, segments and/or truncations thereof. For example, a sequence of human NY-ESO-1 can be found in login number: 1485 of GeneBank.

In the present application, a term "PD-1" can be used interchangeably with "PD1", for example, "PD-1 antibody" can be used interchangeably with "PD1 antibody".

In the present application, a term "medicine product" generally refers to a preparation that allows a biological activity of an active component to exit in an effective form, and does not include other components with an unacceptable toxicity to a subject to whom the preparation is to be administered. In certain embodiments, these preparations can include the active component of the medicine and a medical acceptable carrier. In some embodiments, the medicine product includes the medicine product that is used by parenteral, transdermal, intracavitary, intraarterial, intrathecal and/or intranasal administration or is directly injected into tissues. The medicine product can be administered by different ways, such as intravenous, intraperitoneal, subcutaneous, intramuscular, topical or intradermal administration.

In the present application, a term "medical acceptable" generally refers to an adjuvant that, within a scope of reasonable medical judgment, is suitable for use in contact with the tissues of human and animals without excessive toxicity, irritation, allergic reaction or other problems or complications, and has a reasonable benefit/risk ratio. In some embodiments, a medical acceptable adjuvant can refer to those adjuvants approved by regulatory organizations (such as U.S. Food and Drug Administration, China Food and Drug Administration, or European Medicines Agency) or listed in generally recognized pharmacopoeias (such as U.S. Pharmacopoeia, China Pharmacopoeia, or European Pharmacopoeia) for using for animals (especially for human). In the present application, the medical acceptable adjuvant can be an aluminum based adjuvant, a mineral salt adjuvant, a tension and activity adjuvant, a bacterial derived adjuvant, an emulsion adjuvant, a liposome adjuvant, a cytokine adjuvant, a carbohydrate adjuvant, a DNA and RNA oligomer adjuvant and others.

In the present application, a term "combination" is also called as "co-administration", usually refers to administration before, or after, or at the same time with another medicine component. Two or more medicine components used in combination with each other can be administrated by a same administration method or by different administration methods, and can be administrated at the same time or sequentially. For example, a first therapeutic agent used in combination can be the attenuated oncolytic virus strain/the oncolytic virus vaccine, and a second therapeutic agent used in combination can be the immune checkpoint inhibitor. The combination further can include a third or even more therapeutic agents.

In the present application, a term "prevention" generally refers to preventing a occurrence, a onset, a recurrence and/or a spread of a disease or one or more symptoms thereof by taking certain measures in advance. In the present application, a term "treatment" generally refers to eliminating or alleviating the disease, or one or more symptoms related to the disease. In certain embodiments, "treatment" generally refers to administrating one or more medicines to patients suffering from this disease to eliminate or alleviate the disease. In certain embodiments, "treatment" can be administrating the pharmaceutical composition and/or the medicine product in the presence or absence of other medicines after onset of the symptoms of a specific disease. For example, the occurrence, a development, the recurrence and/or a metastasis of the tumor is prevented by using the pharmaceutical composition and/or the medicine product in the present application.

In the present application, a term "include" generally refers to including explicitly specified features, but not excluding other elements.

In the present application, a term "homology" generally refers to the amino acid sequence or a nucleic acid sequence that has certain homology with a compared amino acid sequence and a compared nucleic acid sequence. The term "homology" can be equated with sequence "identity". Homologous sequences can include the amino acid sequences that are at least about 80%, at least about 85%, at least about 90%, at least about 99.1%, at least about 99.2%, at least about 99.3%, at least about 99.4%, at least about 99.5%, at least about 99.6%, at least about 99.7%, at least about 99.8% or at least about 99.9% the same as the subject sequence. Generally, the homologs include active sites and the like that are the same as the subject amino acid sequence. Homology can be considered in terms of similarity (that is, amino acid residues with similar chemical properties/functions), or expressed in terms of sequence identity.

Invention Descriptions

1. A medicine for resisting a tumor or treating a cancer prepared by using an attenuated oncolytic virus strain, wherein the attenuated oncolytic virus strain is prepared by engineering a matrix protein M of an oncolytic virus, and a gene sequence of an engineered matrix protein M is shown in SEQ ID NO: 3; the medicine includes both an attenuated oncolytic virus strain and an immune checkpoint inhibitor.

2. The medicine for resisting a tumor or treating a cancer prepared by using an attenuated oncolytic virus strain according to embodiment 1, wherein the attenuated oncolytic virus strain is based on a VSV MuddSummer subtype strain, and is obtained after at least the following site-directed genic mutation: mutating of methionine at position 51 into arginine; knocking out of leucine-encoding bases at position 111; mutating of valine at position 221 into phenylalanine; and, mutating of serine at position 226 into arginine.

3. The medicine for resisting a tumor or treating a cancer prepared by using an attenuated oncolytic virus strain according to embodiment 1 or 2, wherein the attenuated oncolytic virus strain is prepared into an oncolytic virus vaccine, and then into a medicine.

4. The medicine for resisting a tumor or treating a cancer prepared by using an attenuated oncolytic virus strain according to embodiment 3, wherein the oncolytic virus vaccine is prepared by inserting an antigen into the attenuated oncolytic virus strain.

5. The medicine for resisting a tumor or treating a cancer prepared by using an attenuated oncolytic virus strain according to embodiment 4, wherein the antigen is a specific tumor antigen.

6. The medicine for resisting a tumor or treating a cancer prepared by using an attenuated oncolytic virus strain according to embodiment 5, wherein the antigen is one selected from a group consisting of: NY-ESO-1, gp33, gp100, TX103, Mucin-1, WT-1, MART-1, MAGE A1, MAGE A3, MAGE A4, MAGE B2, PRAME, SURVIVIN, MART-1, col6A3, tyrosinase, T antigen, SLC45A2, VCX/Y, HPV, alpha fetoprotei, carcinoembryonic antigen, CA 125, Her2, dopachrome tautomerase, BAGE protein, GAGE protein, survivin, tyrosinase, SSX2, cyclin-A1, KIF20A, MUC5AC, Meloe, Lengsin, kallikrein4, IGF2B3 and glypican 3.

7. The medicine for resisting a tumor or treating a cancer prepared by using an attenuated oncolytic virus strain according to embodiment 1 or 2, wherein the immune checkpoint inhibitor is one selected from a group consisting of: anti-PD-1 antibody, anti-PD-L1 antibody, anti-CTLA4 antibody, anti-LAG-3 antibody, anti-TIM-3 antibody and anti-SIGLEC15 antibody.

8. The medicine for resisting a tumor or treating a cancer prepared by using an attenuated oncolytic virus strain according to embodiment 1 or 2, wherein the immune checkpoint inhibitor is released in a body before the oncolytic virus vaccine.

9. The medicine for resisting a tumor or treating a cancer prepared by using an attenuated oncolytic virus strain according to embodiment 1 or 2, wherein the tumor or the cancer is one selected from a group consisting of: head and neck cancer, melanoma, soft tissue sarcoma, breast cancer, esophageal cancer, lung cancer, ovarian cancer, bladder cancer, liver cancer, cervical cancer, neuroblastoma, synovial sarcoma, and round cell liposarcoma.

The present application provides the medicine that can effectively treat various kinds of tumors, and the medicine includes both the oncolytic virus vaccine and the immune checkpoint inhibitor.

A preparation method of the oncolytic virus vaccine is as follows: inserting a gene or a gene segment of NY-ESO-1 into an attenuated oncolytic virus strain. Specifically, the preparation method includes the following steps.

1. Preparing the attenuated oncolytic virus strain. Selecting the vesicular stomatitis virus (VSV), specifically selecting the vesicular stomatitis virus Indiana strain and the VSV MuddSummer subtype strain; a gene sequence of the M protein is shown in SEQ ID NO: 1, and an amino acid sequence of the M protein is shown in SEQ ID NO: 2.

2. Site-directed genic mutation on a gene of the matrix protein M of the vesicular stomatitis virus. The mutation sites include: (1) methionine (M) at position 51 is mutated into arginine (R); (2) leucine(L)-encoding bases at position 111 is knocked out; (3) valine (V) at position 221 is mutated into phenylalanine (F); (4) serine (S) at position 226 is mutated into arginine (R). The vesicular stomatitis virus after the mutation is numbered as: JBS003, and named as: XN2-M51R-□L111-V221F-5226R; a gene sequence of the M protein of the vesicular stomatitis virus after the mutation is shown in SEQ ID NO: 3, and an amino acid sequence of the M protein of the vesicular stomatitis virus after the mutation is shown in SEQ ID NO: 4.

Compared with the wild type VSV and other VSV attenuated strains, JBS003 is safer, and can be used as a carrier (skeleton) for antigens, cytokines and other substances, and can be used as a vaccine or a medicine after being combined with the antigens, the cytokines and other substances. Meanwhile, JBS003 can also be directly used as a medicine applied in tumor immunotherapy without being combined with other substances, and a treatment effect thereof is better than that of the wild type VSV and other VSV attenuated strains.

3. Inserting a gene or a gene segment of NY-ESO-1. Inserting a gene capable of expressing the NY-ESO-1 between a G protein and a L protein of JBS003 to construct the oncolytic virus vaccine, which is numbered as: JBS004.

NY-ESO-1 (New York esophageal squamous cell cancer 1) belongs to a cancer-testis antigen (CTA) family, and is expressed in testis, ovaries and various tumor tissues, but not expressed in other normal tissues. It is a tumor specific antigen with the strongest immunogenicity. Expression abundances of NY-ESO-1 in different tumor tissues are different. The tumors with higher protein expression are myxoid round cell liposarcoma (89%~100%), neuroblastoma (82%), synovial sarcoma (90%), melanoma (46%), and ovarian cancer (43%). NY-ESO-1 antigen is immunogenic and safe, and is a clinical dominant antigen for immunotherapy.

At present, recurrent and metastatic head and neck squamous cell carcinoma, melanoma, soft tissue sarcoma, breast cancer, esophageal cancer, lung cancer, ovarian cancer, bladder cancer, liver cancer, cervical cancer, neuroblastoma and etc. still cannot be effectively treated. JIB S004 oncolytic virus vaccine constructed by introducing NY-ESO-1 can efficiently induce a specific anti-tumor immune response of a body in a peripheral lymphatic system and the tumor tissues. Test shows that in an immunotherapy for anti tumors, especially in the treatment of the above cancers and tumors, the oncolytic virus vaccine has obvious advantages in immunogenicity, effectiveness, targeting, safety and tolerance.

JBS003 attenuated oncolytic virus strain or JBS004 oncolytic virus vaccine can be used separately as a medicine for treating tumors. A use method is: intratumorally injecting or intravenously injecting JBS003 attenuated oncolytic virus strain or JBS004 oncolytic virus vaccine. A intratumoral injection refers to injecting into a corresponding tumor site in the body of a tumor-bearing mammal by taking a small amount of multiple injections.

4. Using JBS004 oncolytic virus vaccine in combination with the immune checkpoint inhibitor as the medicine for treating tumors. The immune checkpoint inhibitor includes: PD-1, PD-L1, CTLA-4, LAG-3, TIM-3, SIGLEC15 antibody and etc. Preferably, the immune checkpoint inhibitor is PD-1 or PD-L1 antibody. For the convenience of comparison and operation, the PD-1 antibody is used in the following embodiments.

A use method of the medicine is as follows: providing (intratumorally injecting or intravenously injecting) the oncolytic virus or the oncolytic virus vaccine in a small amount and multiple times. In some embodiment, an administration order is: administrating the immune checkpoint inhibitor first, and then administrating the oncolytic virus or the oncolytic virus vaccine. Preferably, an injection method of the immune checkpoint inhibitor is an intraperitoneal injection or the intravenous injection; and preferably, an administration method of the oncolytic virus or the oncolytic virus vaccine is the intratumoral injection or the intravenous injection.

On one hand, the present application provides the pharmaceutical composition, which includes the attenuated oncolytic virus strain and the immune checkpoint inhibitor; in which, the attenuated oncolytic virus strain is a VSV MuddSummer subtype strain with a matrix protein M subjected to an engineering, wherein the engineering includes knocking out of leucine-encoding bases at position 111 of an amino acid sequence of the matrix protein M. For example, comparing the matrix protein M of the attenuated oncolytic virus strain with a matrix protein M of the VSV MuddSummer subtype strain, the leucine-encoding bases at position 111 of an amino acid sequence thereof is knocked out. For example, an amino acid sequence of the matrix protein M of the attenuated oncolytic virus strain is shown in SEQ ID NO: 7.

In certain embodiments, the matrix protein M of VSV MuddSummer subtype strain includes the nucleic acid sequence shown in SEQ ID NO: 1. In certain embodiment, the matrix protein M of the VSV MuddSummer subtype strain includes the amino acid sequence shown in SEQ ID NO: 2.

In the present application, the mutation of the gene of the matrix protein M of the attenuated oncolytic virus strain can further include mutating of methionine at position 51 of the amino acid sequence into arginine. For example, comparing the matrix protein M of attenuated oncolytic virus strain with the matrix protein M of the VSV MuddSummer subtype strain, the leucine-encoding bases at position 111 is knocked out and methionine at position 51 is mutated into arginine. For example, the amino acid sequence of the matrix protein M of attenuated oncolytic virus strain is shown in SEQ ID NO: 8.

In the present application, the mutation of the gene of the matrix protein M of the attenuated oncolytic virus strain can further include mutating of valine at position 221 of the amino acid sequence into phenylalanine. For example, comparing the matrix protein M of the attenuated oncolytic virus strain with the matrix protein M of the VSV MuddSummer subtype strain, the leucine-encoding bases at position 111 is knocked out and valine at position 221 is mutated into phenylalanine. For example, the amino acid sequence of the matrix protein M of the attenuated oncolytic virus strain is shown in SEQ ID NO: 9.

In the present application, the mutation of the gene of the matrix protein M of the attenuated oncolytic virus strain can further include mutating of serine at position 226 of the amino acid sequence into arginine. For example, comparing the matrix protein M of the attenuated oncolytic virus strain with the matrix protein M of the VSV MuddSummer subtype strain, the leucine-encoding bases at position 111 is knocked out and serine at position 226 is mutated into arginine. For example, the amino acid sequence of the matrix protein M of the attenuated oncolytic virus strain is shown in SEQ ID NO: 10. For example, comparing the matrix protein M of the attenuated oncolytic virus strain with the matrix protein M of the VSV MuddSummer subtype strain, the leucine-encoding bases at position 111 is knocked out, valine at position 221 is mutated into phenylalanine and serine at position 226 is mutated into arginine. For example, the amino acid sequence of the matrix protein M of the attenuated oncolytic virus strain is shown in SEQ ID NO:11. For example, comparing the matrix protein M of the attenuated oncolytic virus strain with the matrix protein M of VSV MuddSummer subtype strain, methionine at position 51 is mutated into arginine, the leucine-encoding bases at position 111 is knocked out, valine at position 221 is mutated into phenylalanine and serine at position 226 is mutated into arginine. For example, the amino acid sequence of the matrix protein M of the attenuated oncolytic virus strain is shown in SEQ ID NO: 4.

In the present application, the immune checkpoint inhibitor can be one selected from a group consisting of: anti-PD-1 antibody, anti-PD-L1 antibody, anti-CTLA4 antibody, anti-LAG-3 antibody, anti-TIM-3 antibody and anti-SIGLEC15 antibody.

On the other hand, the present application further provides the pharmaceutical composition, which includes the oncolytic virus vaccine and the immune checkpoint inhibitor, and the oncolytic virus vaccine is prepared by using the attenuated oncolytic virus strain described in the present application. In certain embodiments, the oncolytic virus vaccine is prepared by inserting the antigen into the attenuated oncolytic virus strain. For example, the antigen can be one selected from a group consisting of: NY-ESO-1, gp33, gp100, TX103, Mucin-1, WT-1, MART-1, MAGE A1, MAGE A3, MAGE A4, MAGE B2, PRAME, SURVIVIN, MART-1, col6A3, tyrosinase, T antigen, SLC45A2, VCX/Y, HPV, alpha fetoprotei, carcinoembryonic antigen, CA 125, Her2, dopachrome tautomerase, BAGE protein, GAGE protein, survivin, tyrosinase, SSX2, cyclin-A1, KIF20A, MUC5AC, Meloe, Lengsin, kallikrein4, IGF2B3 and glypican 3.

In certain embodiment, the oncolytic virus vaccine is prepared by inserting a tumor-associated antigen into the VSV attenuated strain of which the matrix protein M has a ΔL111 mutation.

In certain embodiment, the oncolytic virus vaccine is prepared by inserting the tumor-associated antigen into the VSV attenuated strain of which the matrix protein M has ΔL111 and M51R mutations.

In certain embodiment, the oncolytic virus vaccine is prepared by inserting the tumor-associated antigen into the VSV attenuated strain of which the matrix protein M has ΔL111 and V221F mutations.

In certain embodiment, the oncolytic virus vaccine is prepared by inserting the tumor-associated antigen into the VSV attenuated strain of which the matrix protein M has ΔL111 and S226R mutations.

In certain embodiment, the oncolytic virus vaccine is prepared by inserting the tumor-associated antigen into the VSV attenuated strain of which the matrix protein M has ΔL111, V221F and S226R mutations.

In certain embodiment, the oncolytic virus vaccine is prepared by inserting the tumor-associated antigen into the VSV attenuated strain of which the matrix protein M has ΔL111, M51R, V221F and S226R mutations.

In the present application, the immune checkpoint inhibitor in the pharmaceutical composition can be one selected from a group consisting of: anti-PD-1 antibody, anti-PD-L1 antibody, anti-CTLA4 antibody, anti-LAG-3 antibody, anti-TIM-3 antibody and anti-SIGLEC15 antibody. In some embodiment, the immune checkpoint inhibitor is PD-1 antibody (anti-PD-1 antibody). For example, a variable region of heavy chain of the PD-1 antibody can include an amino acid sequence shown in SEQ ID NO: 12. For example, a variable region of light chain of the PD-1 antibody can include an amino acid sequence shown in SEQ ID NO: 13.

In the present application, the immune checkpoint inhibitor is released in the body before the oncolytic virus vaccine.

In the present application, the pharmaceutical composition can be used for resisting a tumor or treating a cancer. In the present application, the tumor or the cancer is one selected from a group consisting of: head and neck cancer, melanoma, soft tissue sarcoma, breast cancer, esophageal cancer, lung cancer, ovarian cancer, bladder cancer, liver cancer, cervical cancer, neuroblastoma, synovial sarcoma, and round cell liposarcoma.

On the other hand, the present application further provides the medicine product, which includes the pharmaceutical composition and the optional medical acceptable carrier.

In the present application, the attenuated oncolytic virus strain can be prepared through a virus rescue process. Specifically, the process can include inoculating BHK-21 cells by infecting with a poxvirus expressing a RNA polymerase, preparing a plasmid transfection premix with an expression plasmid cloning VSV N, VSV P and VSV L gene, as well as the expression plasmid cloning VSV M or the expression plasmid cloning mutant VSV M, and lipofectamine transfecting, so as to obtain a mutant strain.

In the present application, the components in the pharmaceutical composition and/or the medicine product can be placed in one container, or in different containers respectively.

In the present application, the components in the pharmaceutical composition and/or the medicine product can be mixed together, or placed respectively.

The present application further provides a use of the attenuated oncolytic virus strain/oncolytic virus vaccine in combination with the immune checkpoint inhibitor in preparing the medicine.

The present application further provides a use of the expression carrier of the attenuated oncolytic virus strain/the oncolytic virus vaccine in combination with the immune checkpoint inhibitor in preparing the medicine.

In some embodiments, the attenuated oncolytic virus strain/the oncolytic virus vaccine and the immune checkpoint inhibitor can be administrated at the same time. “Administrated at the same time” can be administrated after mixing the components or administrated respectively. The administrations can be performed in a same method, for example administrating to a same vein or other blood vessels, or in different methods, for example intravenously administrating and the intratumorally administrating at the same time.

In some embodiments, the attenuated oncolytic virus strain/the oncolytic virus vaccine and the immune checkpoint inhibitor can be administrated sequentially. The administration order can be: administrating the attenuated oncolytic virus strain/the oncolytic virus vaccine first, and then administrating the immune checkpoint inhibitor; or administrating the immune checkpoint inhibitor first, and then administrating the attenuated oncolytic virus strain/the oncolytic virus vaccine. The administrations can be performed in a same method, or in different methods. All components can be administrated at one time or multiple times. In certain embodiments, “administrated sequentially” can be administered at any time intervals, including minute, hour, day, week, month or year. In certain embodiments, “administrated sequentially” refers to respectively administrated at time interval of 2 minutes, 5 minutes, 10 minutes, 30 minutes, 1 hour, 6 hours, 8 hours, 12 hours, 24 hours, 36 hours, 48 hours, 3 days, 4 days, 5 days, 6 days, 1 weeks, 2 weeks, 3 weeks, 1 month, 6 weeks, 2 months, 3 months, 4 months, 5 months or 6 months.

In some embodiments, an administrated dose can be any dose.

In some embodiments, the administrated dose can be a therapeutic effective amount.

In some embodiments, the attenuated oncolytic virus strain/the oncolytic virus vaccine can be formulated for an intratumoral administration. In some embodiments, the attenuated oncolytic virus strain/the oncolytic virus vaccine can be formulated for an intravenous administration.

In some embodiments, the immune checkpoint inhibitor can be formulated for a systemic administration. In some embodiments, the immune checkpoint inhibitor can be formulated for a topical administration.

Not limited by any theories, the following examples are only used to illustrate the various technical solutions in the present application, not to limit the scope of the present application.

EXAMPLES

Example 1: Construction and Effect of Site-Directed Mutated Attenuated Strain 1. According to the methods in Table 1, a site-directed mutation was performed on the matrix protein M of vesicular stomatitis virus Indiana strain, and then 7 groups mutated attenuated strains were obtained. As a control, the group without gene mutation was numbered as JBS000.

TABLE 1 mutation situation in each group

| No. of Attenuated Strain | Name of Vaccine | Mutation Site and Amino Acid after Mutation | No. of Mutation Sites |
|---|---|---|---|
| JBS000 | XN2-WT | / | / |
| JBS001 | XN2-M51R | methionine M at position 51 was mutated into arginine R | 1 |
| JBS002 | XN2-M5IR-□L111 | 1.methionine M at position 5 Iwas mutated into arginine R; 2.1eucine L-encoding bases at position 111 was knocked out. | 2 |
| JBS003 | XN2-M51R-□L111-V221F-S226R | 1.methionine M at position 5 Iwas mutated into arginine R; 2.1eucine L-encoding bases at position 111 was knocked out; 3.valine V at position 221 was mutated into phenylalanine F; 4.serine S at position 226 was mutated into arginine R. | 4 |
| JBS008 | XN2 -□L111 | leucine L-encoding bases at position 111 was knocked out | 1 |
| JBS009 | XN2-□LI11-V221F | 1.leucine L-encoding bases at position ill was knocked out; 2.valine V at position 221 was mutated into phenylalanine F. | 2 |
| JBS010 | XN2-DLI11-S226R | 1.leucine L-encoding bases at position ill was knocked out; 2.serine S at position 226 was mutated into arginine R. | 2 |
| JBS014 | XN2 -□L111-V221F-S226R | 1.leucine-encoding bases at position ill was knocked out; 2.valine V at position 221 was mutated into phenylalanine F; 3.serine S at position 226 was mutated into arginine R. | 3 |

Specifically, a construction method of the attenuated strain was a conventional technology in the field, which was simply described as follows.

(1) Constructing the plasmids. Using pVSV-XN2 plasmid as a template, and different mutation sites described in Table 1 were introduced by PCR method. PCR was performed by using the plasmids and primers of the mutation sites together, and PCR products were subjected to 1% agarose gel electrophoresis, and then a extraction to cut gels was performed by using a gel extraction kit, thereby the plasmids with different mutations of the matrix protein M were obtained.

(2) Virus rescue. At MOI=5, BHK-21 cells were inoculated by inflecting with poxvirus vTF7-3 expressing T7 RNA polymerase. After 1 hour of the infection, BHK-21 cells were rinsed once with DPBS buffer. Then, a plasmid transfection premix was prepared, and the plasmid transfection premix specifically included: pBS-N, pBS-P, pBS-L and the mutated plasmid prepared in step (1). In which, pBS-N, pBS-P and pBS-L respectively refers to the expression plasmid cloned with VSV N, VSV P and VSV L protein genes, and respectively expresses N, P and L proteins needed for the virus rescue. A plasmid transfection was performed according to a method described in a user manual of lipofectamine 2000. After 4 hours, a fresh DMEM complete medium containing 10% of fetal bovine serum was replaced; after 48 h, a supernate was collected, and then the poxvirus was removed by filtering through a 0.22 μm filter membrane. A filtrate was added into the fresh BHK-21 cells; then cell pathological changes were observed everyday, and a supernate was collected when the cells occurred pathological changes. After confirmed successfully by using RTPCR, the virus was purified by virus plaque assay. Thereby, the attenuated strain was obtained.

(3) M protein sequencing. A viral genome RNA was extracted with Trizol kit, and a reverse transcription reaction was performed with random primers, and then a reverse transcribed cDNA was subjected to PCR with the primer designed for the gene sequence of M protein. Sequences of the primer were 5'-AAAAAAGTAACAGATATCAC-3' (SEQ ID NO: 5); 5'-ACATTTTTCCAGTTTCCTTTTTGG-3'(SEQ ID NO: 6). A product was extracted after 1% agarose gel electrophoresis and sent to a sequencing company for sequencing.

2. Ability of different attenuated strains to infect cells in vitro. 200 pfu JBS000, 200 pfu JBS001, 200 pfu JBS002, 200 pfu JBS003, 200 pfu JBS008, 200 pfu JBS009, 200 pfu JBS010 and 200 pfu JB 5014 were added into MEF cell (human fibroblast) culture solution and LLC cell (mouse non-small cell lung cancer cell) culture solution respectively, and 50% tissue culture infection dose (TCID50) produced by the attenuated strains in each group was detected. Specifically, a detecting method was as follows.

(1) 3 mL of cell suspension was added into each well of a 6-well culture plate to make a cell number reach $4\times10^5$/well for 6 wells in total, and then cultured for 16 h under a condition of 37° C. and 5% of $CO_2$.

(2) 200 pfu JBS000, 200 pfu JBS001, 200 pfu JBS002, 200 pfu JBS003, 200 pfu JBS008, 200 pfu JBS009, 200 pfu JBS010 and 200 pfu JBS014 were added into each well respectively, and 2 wells were set for normal cell control. At 24 hours, 100 μL of a cell supernate was taken.

(3) 100 μL of Vero cell suspension was added into each well of a 96-well culture plate to make the cell number reach $1\times10^4$/mL, and cultured for 16 h under the condition of 37° C. and 5% of $CO_2$.

(4) The supernate obtained in step (2) was diluted at a 10-fold dilution ratio serially in a 1.5 m LEP tube, a total of 11 titers ranging from $10^{-1}$-$10^{-11}$ were obtained.

(5) The diluted supernates were inoculated into the 96-well culture plate in step (3), and one column (8 wells in total) for each dilution was inoculated, and 100 μL was inoculated in each well. One column for normal cell was set as a control group.

(6) A fluorescence of cells in each well was observed after 48 hours, if there was the fluorescence, then the well was marked with being infected.

Figure 1B:
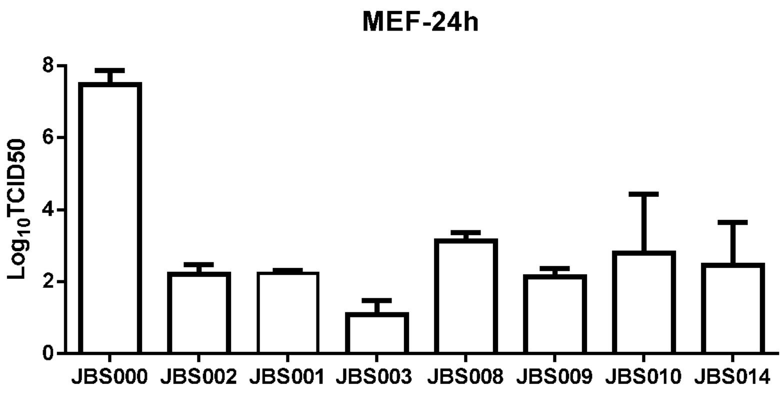

(7) TCID50 was calculated according to Karber method. Results were shown in FIG. 1A and FIG. 1B. A replication and amplification ability of each constructed attenuated oncolytic virus strain in the lung cancer cells (LLC) in vitro was stronger r than that of the attenuated oncolytic virus strain in the normal fibroblasts (MEF). In which, JBS003 had the stronger replication and amplification ability in lung cancer cells (LLC) in vitro, and a number of virus particles produced after 24 hours of the infection was close to that of wild type viruses. However, in the normal fibroblasts (MEF), the replication and infection ability of each attenuated oncolytic virus strain was decreased. Thus, JBS003 carrier has a stronger specific infection ability to the tumor cells.

3. Killing ability of different attenuated strains on cells in vitro. Different cells were infected with a same amount of each attenuated strain in vitro, and a cell viability was detected by MTT method after 24 hours. Specifically, the method was as follows.

(1) 100 μL of cell suspension was added into each well of the 96-well culture plate to make the cell number reach $1\times10^4$/well, and cultured for 16 h under the condition of 37° C. and 5% of $CO_2$. Kinds of detected cells were LLC, MEF and Hela (human tumor cells).

(2) JBS000, JBS001, JBS002, JBS003, JBS008, JBS009, JBS010, and JBS014 were diluted to MOI (multiplicity of infection) of 0.001, 0.01, 0.1, and 1.0 respectively, and each dilution titer was inoculated in 4 wells, and 100 μL was inoculated in each well, then cultured for 40 h under the condition of 37° C. and 5% of $CO_2$.

(3) A supernate in the 96-well culture plate was removed, and the fresh DMED medium was added, then 5 mg/mL MTT solution was added, 20 μL/well. Cultured for 4 h under the condition of 37° C. and 5% of $CO_2$.

(4) The 96-well culture plate was centrifuged for 5 minutes at 2500 g/min and at a room temperature. Then, The supernatant was gently removed using 1 mL disposable sterile syringe.

(5) DMSO was added into each well, 100 μL/well, and placed for 10 minutes at 37° C.

(6) An OD value of each well at a wavelength of 570 nm was measured using a multifunctional microplate reader with shake for 2 minutes.

Figure 2A:
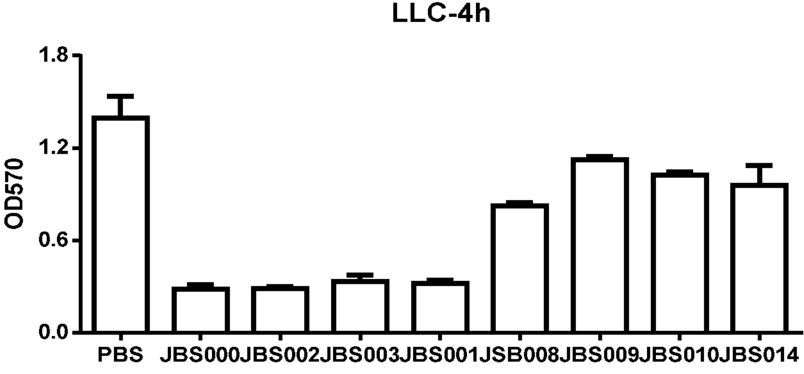
FIGS. 2A-2B are schematic diagrams showing a killing ability of each of attenuated strains to LLC cells and Hela cells in vitro.
Figure 2B:
Figure 2B:
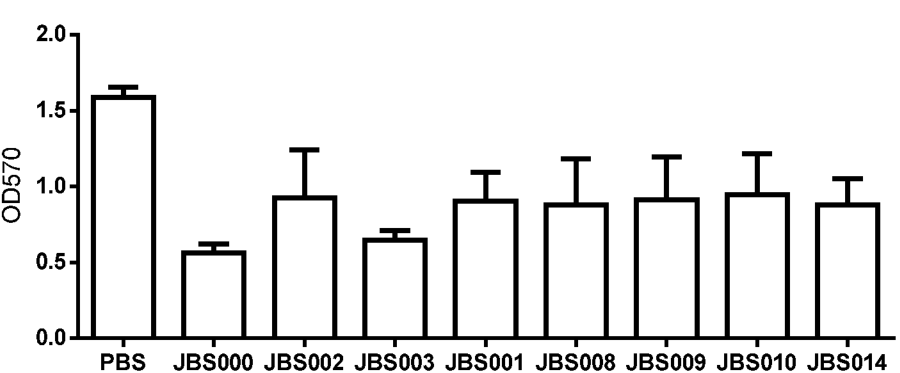
Figure 3:
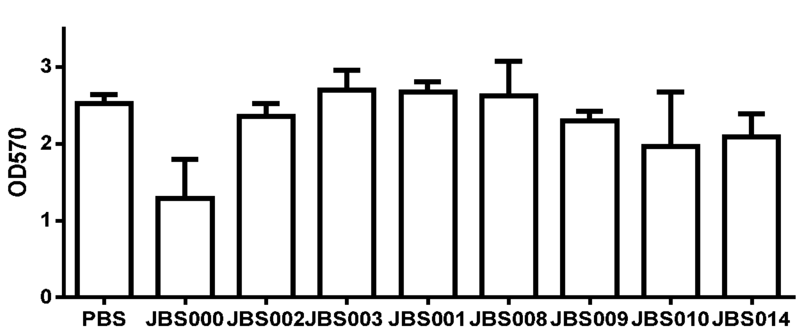
FIG. 3 is a schematic diagram showing a killing ability of each of attenuated strains to MEF cells in vitro.

Results were shown in FIG. 2A, FIG. 2B and FIG. 3. The results indicated that all of the attenuated oncolytic virus strains had a good ability to kill the tumor cells and had no significant killing ability to MEF cells, except for JBS000. That is, in vitro, all of the attenuated strains except JBS000 had specific killing effect on the tumor cells, and had no significant effect on the normal cells.

Figure 4A:
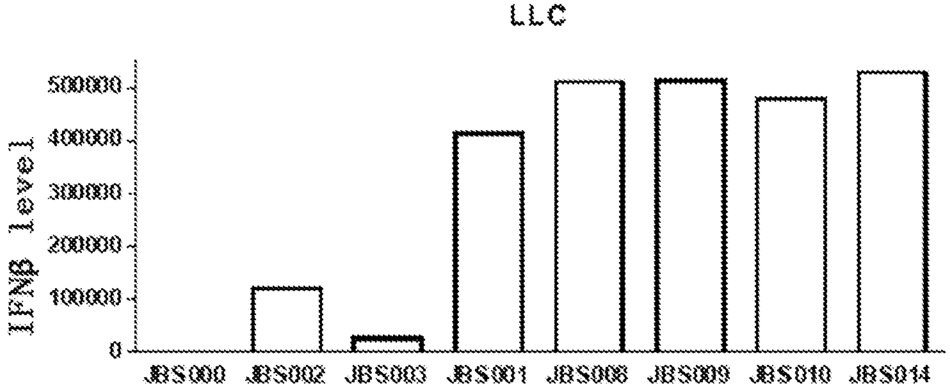
FIGS. 4A-4B are schematic diagrams showing an effect of each of attenuated strains on an expression level of IFN-β in LLC cells and MEF cells in vitro.
Figure 4B:
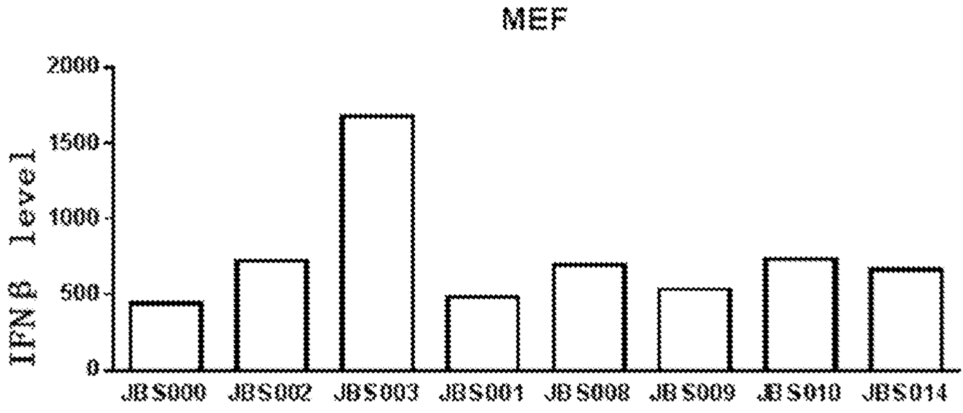

Testing on elimination of different attenuated strains in the cells w using IFN-β as a indicator. The cells were cultured and the attenuated strains were added according to step (1) and (2) in step 3. Then, the cells in each group were broken, and total RNA was extracted from each cell by using TRIzol (Invitrogen), and reverse transcribed into cDNA by using reverse transcription kit of PrimeScript RT Reagent Kit with DNA Eraser (Takara), then dyed with dyestuff of LightCycler 480SYBR Green I Master (Roche), and a Ct value of each gene was detected by using LightCycle 480 quantitative PCR instrument. Relative expression levels of target genes IFN-β and VSV-G were calculated by AA Ct method, and results were shown in FIG. 4. In LLC cell lines, all of the attenuated strains except JBS000 can cause an improvement of an expression level of IFN-β, in which, JBS003 carrier had the lowest regulatory ability; however, in the MEF cells, all of the viruses can improve the expression level of IFN-β, in which, the expression level in JBS003 was highest, which was 3 times in the wild type virus carrier (JBS000). That is, JBS003 was difficult to be eliminated in the tumor cells but easy to be eliminated in the normal cells.

Example 2: Construction and Effect of Oncolytic Virus Vaccine

Figure 5:
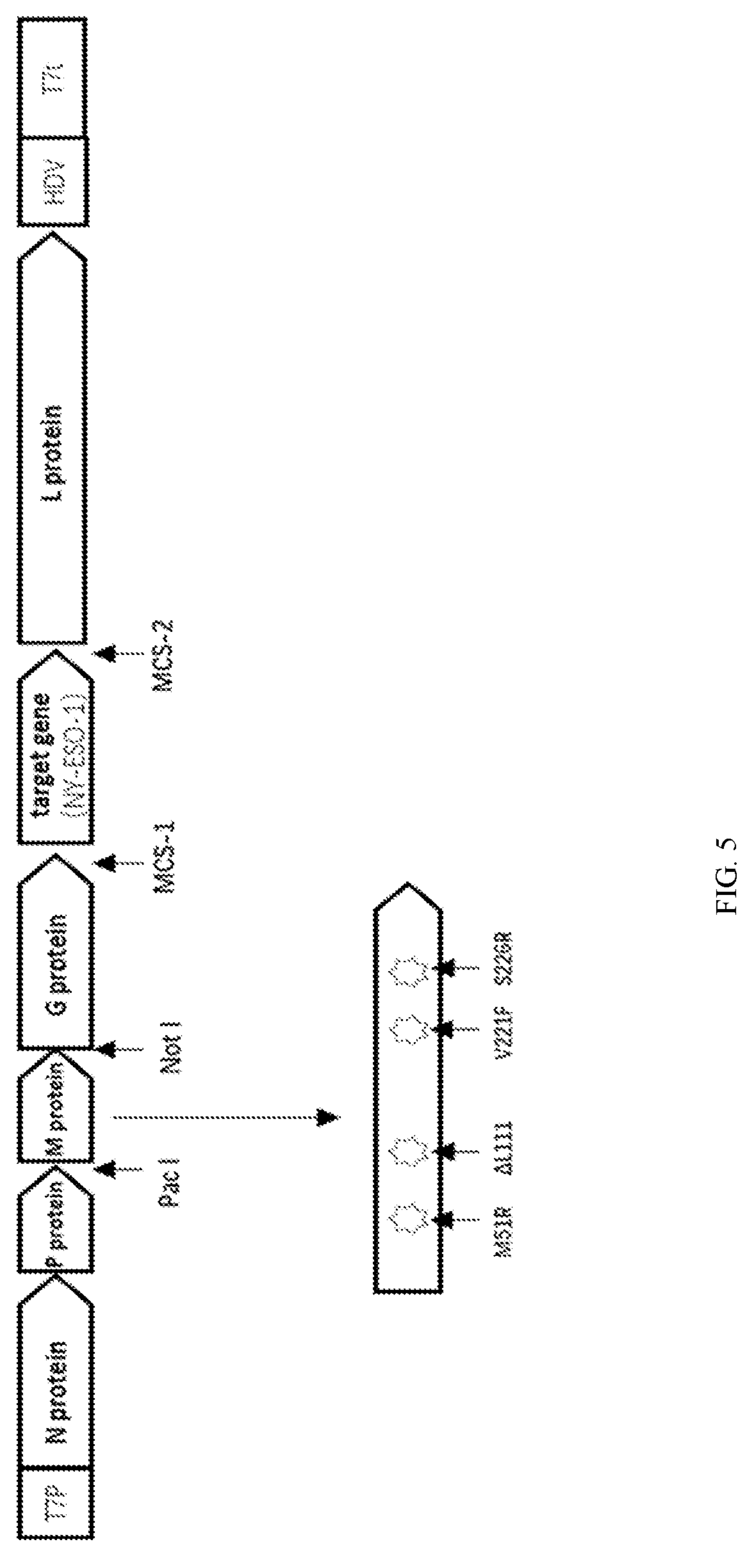
FIG. 5 is a schematic diagram of a construction of an oncolytic virus vaccine.

1. Base on the attenuated strain prepared in Example land the wild type virus, the NY-ESO-1 genes were inserted, then constructed and obtained the oncolytic virus vaccines. A schematic diagram of the construction was shown in FIG. 5, and inserted genes or gene segments in each group were shown in Table 2.

TABLE 2 inserted genes or gene segments in each group

| No. Of Vaccine | Name of Vaccine | Corresponding attenuated strain |
|---|---|---|
| JBS004 | XN2-M51R- □L111-V22 IF- S226R NY-ESO-1 | JBS003+NY-ESO-1 |
| JBS005 | XN2-M51R- □L111-NY-ESO-1 | JBS002+NY-ESO-1 |
| JBS006 | XN2-M51R-NY-ESO-1 | JBS001+NY-ESO-1 |
| JBS007 | XN2-WT-NY-ES0-1 | JBS000+NY-ESO-1 |
| JBS011 | XN2 -□L111-NY-ESO-1 | JBS008+NY-ESO-1 |
| JBS012 | XN2 -□L111-V221F-NY-ESO-1 | JBS009+NY-ESO-1 |
| JBS013 | XN2 -□L111-S226R-NY-ESO-1 | JBS010+NY-ESO-1 |
| JBS015 | XN2 -□LI11- V221F-S226R-NY-ESO-1 | JBS014+NY-ESO-1 |

Specifically, preparation methods of JBS004-JBS007, JBS011-JBS013 and JBS015 were conventional technology in the art, which were described as follows. It should be note that, the following descriptions do not limit that JBS004-JBS007, JBS011-JBS013 and JBS015 can prepared only according to the following methods, but give examples.

(1) Constructing the plasmids of the attenuated strain. Link sequences with restriction enzyme cutting sites Xho I and Mlu I were synthesized artificially, and were inserted into non-coding regions between G protein and L protein of each of the attenuated strains prepared in Example 1 by using biological technology and gene recombination technology, then the plasmids of the attenuated strains were obtained.

(2) Inserting the exogenous gene. Each of the plasmids of the attenuated strains was double digested with Xho I and Mlu I, and then the NY-ESO-1 exogenous gene was inserted to obtain recombinant plasmids of the attenuated strains carrying NY-ESO-1.

(3) Vaccine rescue. The vaccine corresponding to each of the recombinant plasmids of the attenuated strains was rescued by referring to the method of "virus rescue" in Example 1, then the oncolytic virus vaccines were constructed.

2. Treatment effects on LLC-NY-ESO-1 non-small cell lung cancer (transplanted tumors).

136 C57BL/6 mice with no significant difference were selected, and subcutaneously inoculated $2\times10^5$ of LLC cells (lung cancer cells of mouse), and cultured for 9 days under the same and appropriate conditions. On 9th day of the inoculation, when the volume of the transplanted tumor was about 100 $mm^3$, all of the mice were divided into 17 groups (n=8); the mice in a control group (PBS group) were injected with 50 μL of PBS intratumorally, and the remaining 16 groups were treated groups, in which the mice were intratumorally inoculated of JBS000, JBS001, JBS002, JBS003, JBS004, JBS005, JBS006, JBS007, JBS008, JBS009, JBS010, JBS011, JBS012, JBS013, JBS014 and JBS015 respectively, and an administration was performed once every 2 days for 3 times in total, and a single dose was $10^7$ pfu/mouse. From beginning of the administration to an end of the experiment, the volume of the transplanted tumor was recorded every 2 days. The volume ($mm^3$)=(long diameter× short diameter$^2$)/2. A metastatic proportion of the cancer cells was detected by the following detection method: LLC cells have red fluorescent protein, which will show yellow fluorescence under a green fluorescent microscope; when the cancer cells had metastasized to a lung tissue, the lung tissue was placed under the microscope, and fluorescent pictures were taken, and then a gray value of the pictures was analyzed by Image J to analyze a proportion of the lung cancer cells, thereby the metastatic proportion of the cancer cells was obtained.

Figure 6:
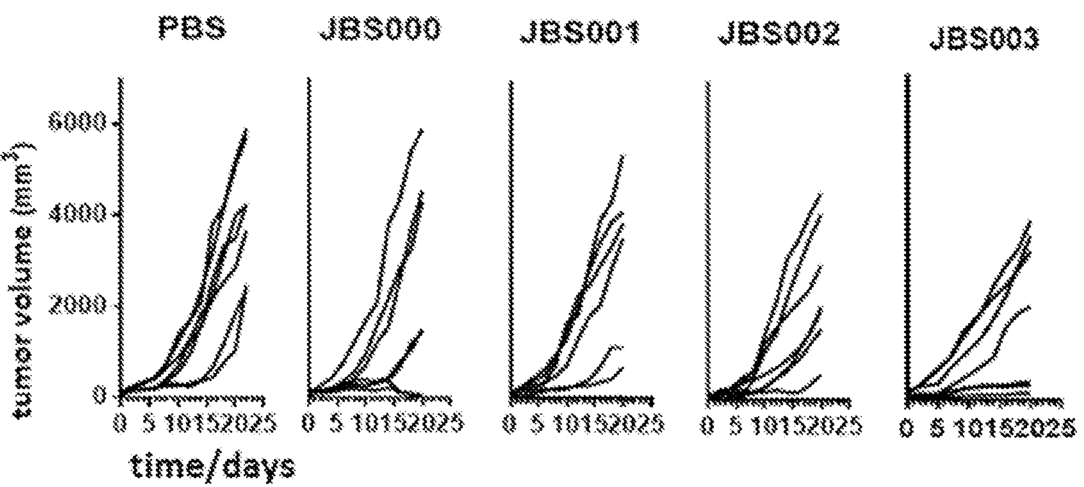
FIG. 6 is a schematic diagram showing an effect of each of attenuated strains on a volume of non-small cell lung cancer (transplanted tumor) in mice.
Figure 7:
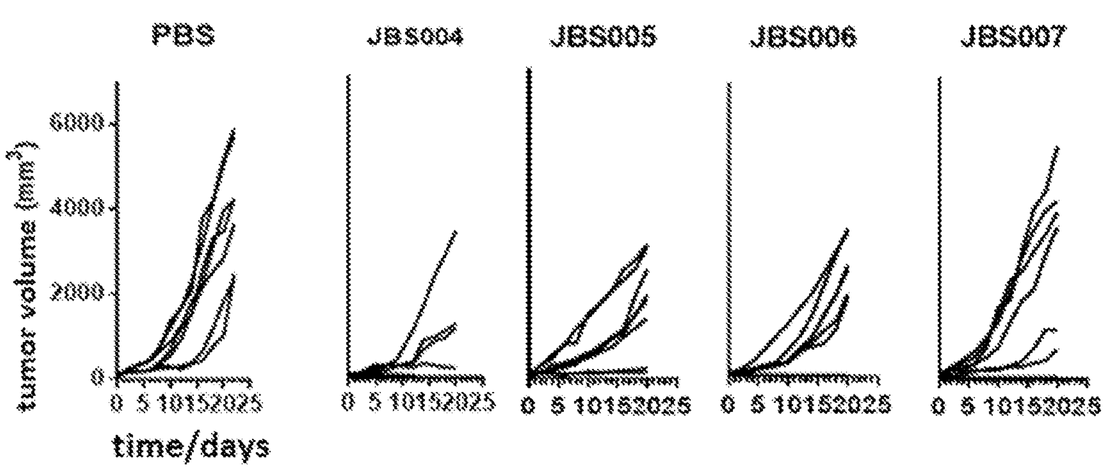
FIG. 7 is a schematic diagram showing an effect of each of vaccines on a volume of non-small cell lung cancer (transplanted tumor) in mice.
Figure 8:
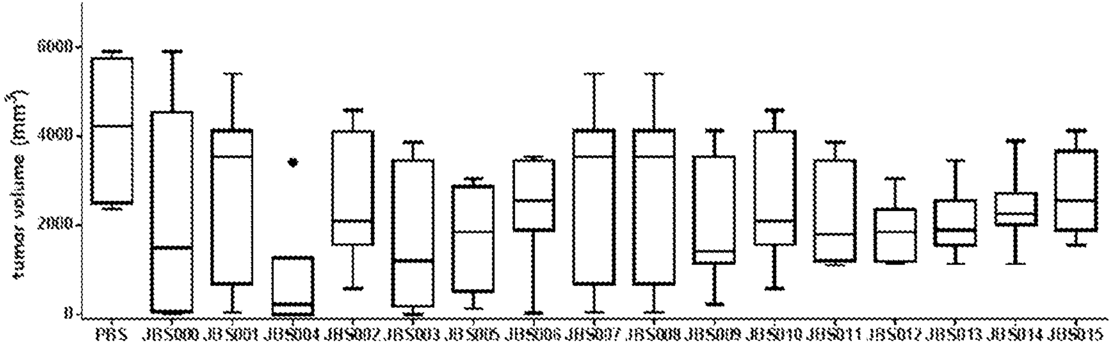
FIG. 8 is a schematic diagram of the volume of non-small cell lung cancer (transplanted tumor) in mice treated with each of attenuated strains and vaccines at an end of an experiment.
Figure 9:
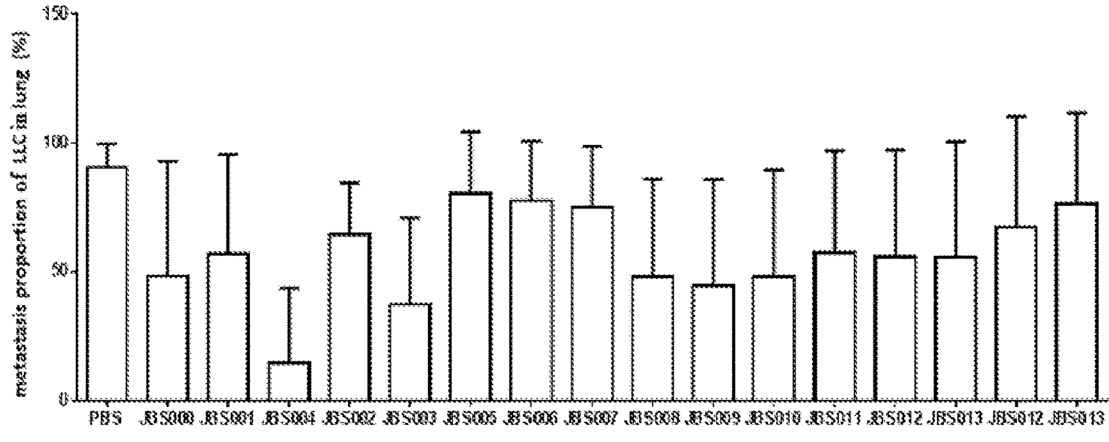
FIG. 9 is a schematic diagram showing an effect of each of attenuated strains and vaccines on a metastasis of non-small cell lung cancer cells in mice.

Changes in the tumor volumes were shown in FIGS. 6-8. Results indicated that all treated groups had certain inhibitory effects on the transplanted tumor. In which, one mouse in JBS003 group was completely cured. The cure rate of JBS004 to the transplanted tumor was 37.5%. The metastasis of cancer cells were shown in FIG. 9. It can be seen from FIGS. 6-9 that there was a certain correlation between the volume of the transplanted tumor and the metastasis proportion in lung. The treatment effect of JBS003 on the metastases in lung was better than that of JBS000 and JBS001; the ability of JBS004 to inhibit or prevent the metastasis of lung cancer cells was better than other groups.

3. Treatment effects on MCA-205-NY-ESO-1 fibrosarcoma (transplanted tumor).

Figure 10:
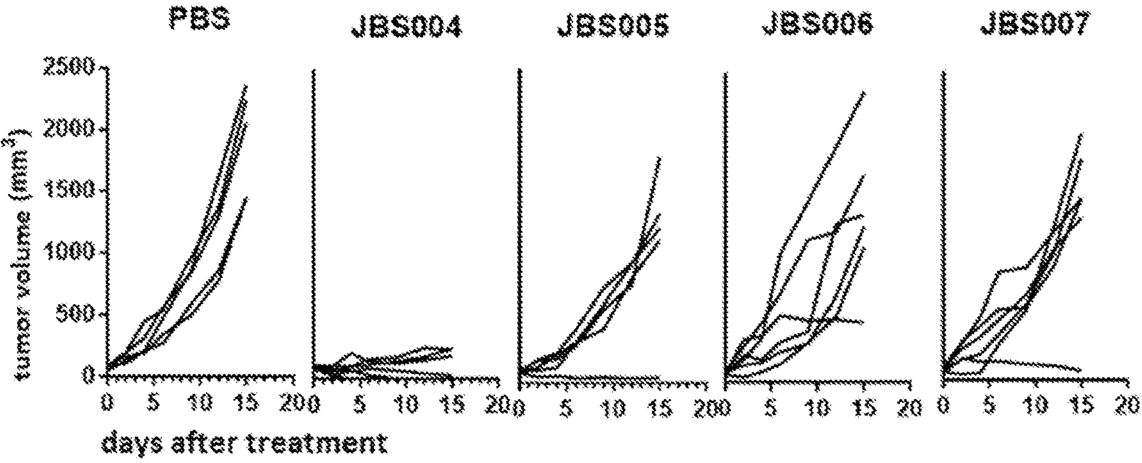
FIG. 10 is a schematic diagram showing an effect of each of vaccines on a volume of fibrosarcoma (transplanted tumor) in mice.
Figure 11:
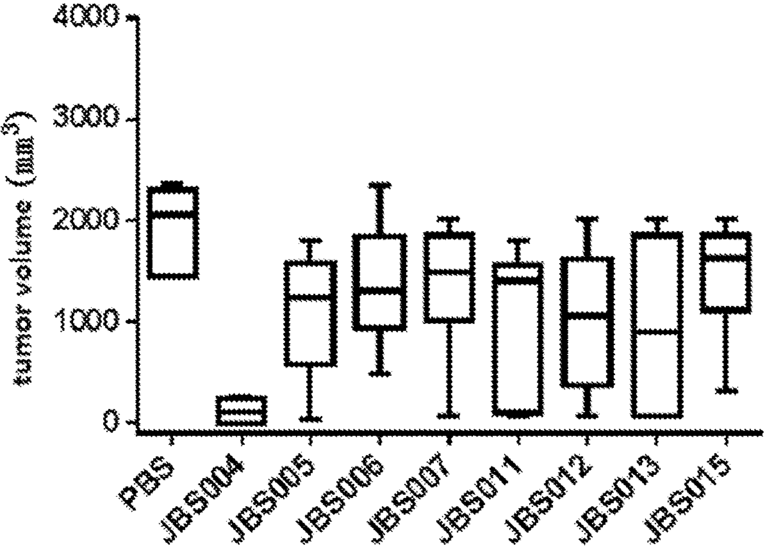
FIG. 11 is a schematic diagram of the volume of fibrosarcoma (transplanted tumor) in mice treated with each of vaccines at the end of the experiment.

The mice were treated according to the method of "treating LLC-NY-ESO-1 non-small cell lung cancer transplanted tumor", and $10^6$ of MCA-205-NY-ESO-1 fibrosarcoma cells were subcutaneously inoculated, and the mice were treated when the volume of the transplanted tumor was about 100 $mm^3$. Similarly, intratumoral injection of 50 μL of PBS as the control group. In the treated groups, JBS004, JBS005, JBS006, JBS007, JBS011, JBS012, JBS013, and JBS015 were intratumorally inoculated respectively; and 6 mice in each group, and the administration was performed once every two days for 3 times in total at the single dose of $10^8$ pfu/mouse. From the beginning of the administration to the end of the experiment, the volume of the transplanted tumor was recorded every 2 days. Results were shown in FIG. 10 and FIG. 11.

The results indicated that all of the treated groups can reduce the tumor volume to a certain extent. After treatment with JBS004, the transplanted tumors in 2 mice were completely eliminated (33.33%), and the tumor volumes of the remaining mice were also well controlled, which were significantly different from the other groups. A total response rate of JBS004 in the treatment of fibrosarcoma was 100%.

4. Treatment effects on B16-F10-NY-ESO-1 melanoma (transplanted tumor).

Figure 12:
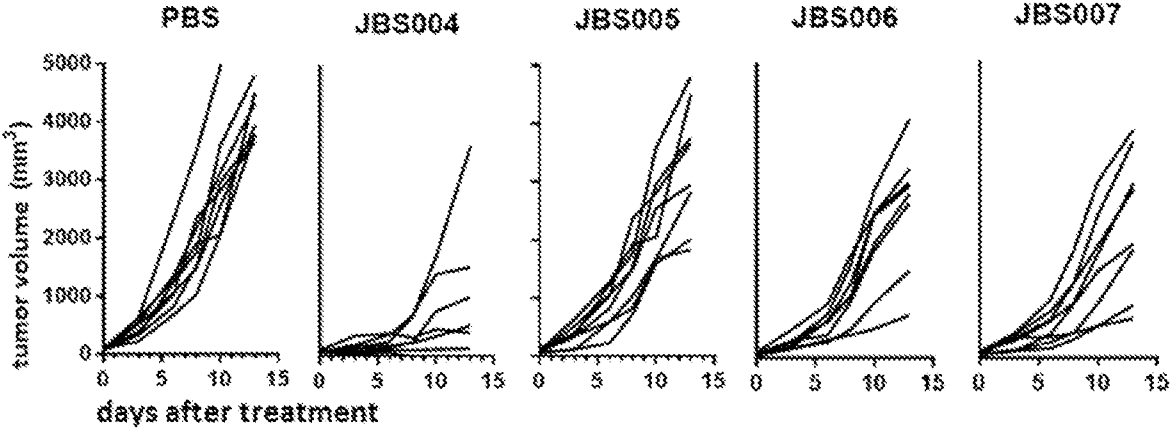
FIG. 12 is a schematic diagram showing an effect of each of vaccines on a volume of melanoma (transplanted tumor) in mice.
Figure 13:
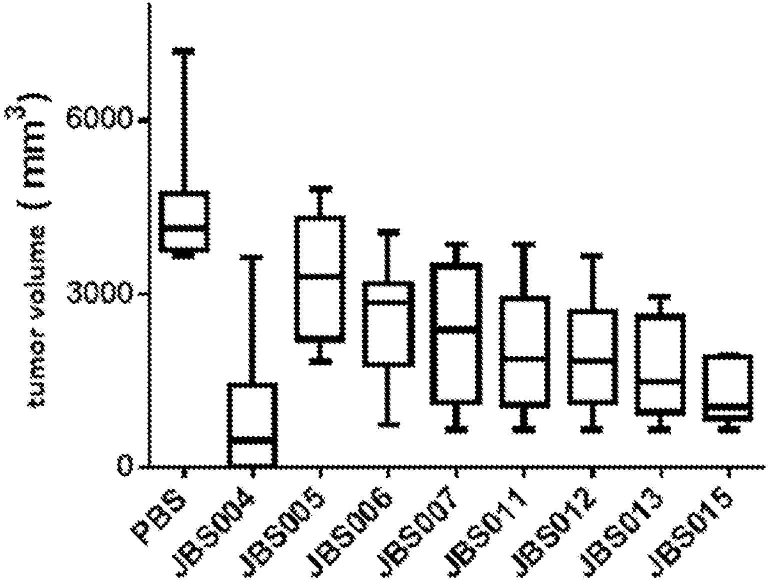
FIG. 13 is a schematic diagram of the volume of melanoma (transplanted tumor) in mice treated with each of vaccines at the end of the experiment.

The mice were treated according to the processing method in the transplanted tumor testing described above, and $2\times10^6$ of B16-F10-NY-ESO-1 melanoma cells were subcutaneously inoculated, and the mice were treated when the volume of the transplanted tumor was about 100 $mm^3$. Similarly, intratumoral injection of 50 μL of PBS as the control group. In the treated groups, JBS004, JBS005, JBS006, JBS007, JBS011, JBS012, JBS013 and JBS015 were intratumorally inoculated respectively, and 6 mice in each group, and the administration was performed once every two days for 3 times in total at the single dose of $10^8$ pfu/mouse. From the beginning of the administration to the end of the experiment, the volume of the transplanted tumor was recorded every 2 days. Results were shown in FIG. 12 and FIG. 13. The results indicated that all of the treated groups had certain treatment effects on melanoma, especially the treatment effect of JBS004 group was the best.

5. Effects of JBS004 at different doses.

Figure 14:
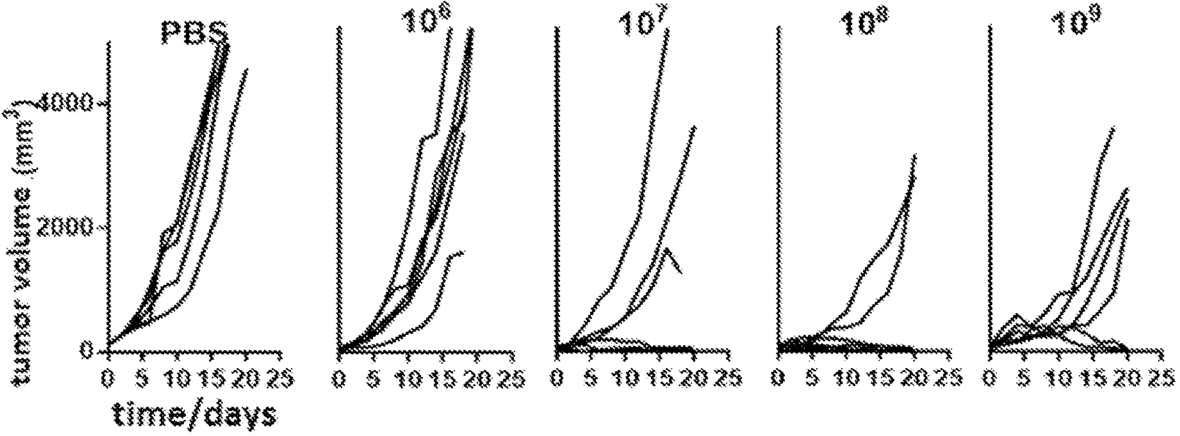
FIG. 14 is a schematic diagram showing an effect of JBS004 at different doses on a volume of non-small cell lung cancer (transplanted tumor) in mice.
Figure 15:
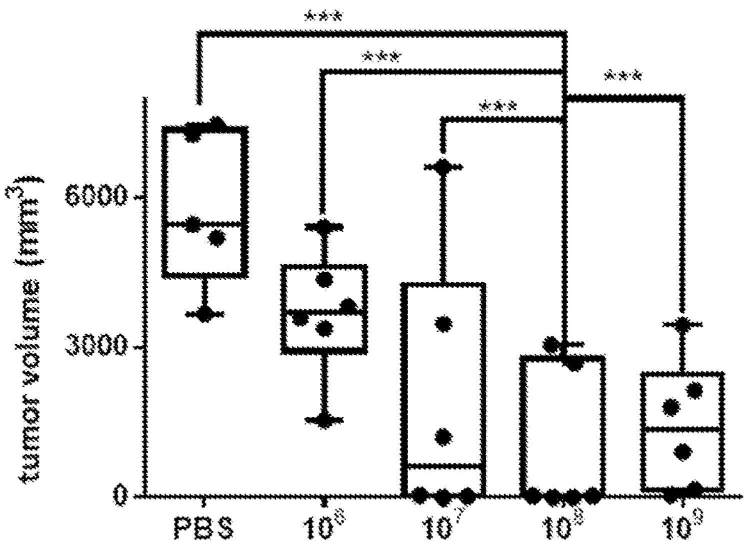
FIG. 15 is a schematic diagram of the volume of non-small cell lung cancer (transplanted tumor) in mice treated with JBS004 at different doses at the end of the experiment.

C57BL/6 mice aged 6-8 weeks and weighed about 18 g were selected, and $2\times10^5$ of LLC cells (lung cancer cells of mouse) were subcutaneously inoculated respectively. On 9th day of the inoculation, when the volume of the transplanted tumor was about 100 $mm^3$, all of the mice were divided into 5 groups with 6 mice in each group; the mice in a control group (PBS group) were injected with 50 μL of PBS intratumorally, and the remaining 4 groups were treated groups, in which the mice were intratumorally inoculated of JBS004 at $10^6$ pfu/mouse, $10^7$ pfu/mouse, $10^8$ pfu/mouse, and $10^9$ pfu/mouse respectively, and the administration was performed once every 2 days for 3 times in total. From the beginning of the administration to the end of the experiment, the volume of the transplanted tumor was recorded every 2 days. Results were shown in FIG. 14 and FIG. 15. At the end of the experiment, the mice were euthanized and autopsied, and the lung tissues of the mice were taken to detect the metastatic proportion of the cancer cells. Results were shown in FIG. 16.

The results indicated that JBS004 at different doses have certain treatment effects on the mice with lung cancer. In which, under the dose of $10^8$ pfu/mouse, the cure rate was 33.33%, and an effective control rate was 33.33%, and a rate of no lung cancer cell metastasis was 66.67%, which was significantly better than other dose groups.

Figures 16, 17:
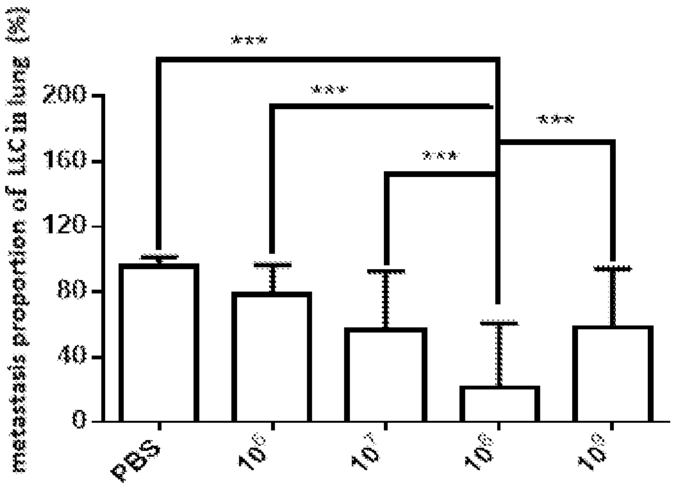
FIG. 16 is a schematic diagram showing an effect of JBS004 at different doses on a metastasis of non-small cell lung cancer cells in mice.
FIG. 17 is a schematic diagram showing an effect of JBS004 at different doses on weight of mice with lung cancer.
Figure 18:
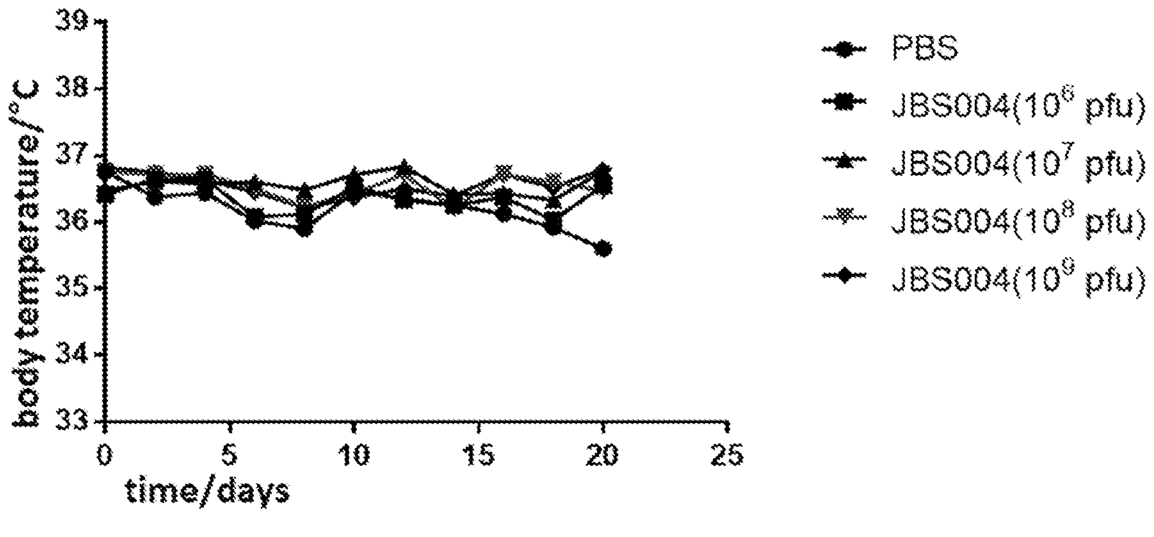
FIG. 18 is a schematic diagram showing an effect of JBS004 at different doses on body temperature of mice with lung cancer.

Additionally, as shown in FIG. 17 and FIG. 18, during the whole experiment, a body temperature and a weight of the mice were kept within a normal range, and there was no abnormal body temperature and the weight, indicating that JBS004 at different doses had no significant effect on the body temperature and the weight of the mice with lung cancer. In terms of the weight, the weight of the mice in the PBS group increased steadily, but the weight of the mice in each of the treated groups increased slowly, which should be related to a reduction of the volume of the transplanted tumor. At the end of the experiment, there was no significant difference in the weight of the mice in each group, which proved that JBS004 was safe.

Example 3: Test Results of Pharmacokinetics and Acute Toxicity of JBS004

Figure 19:
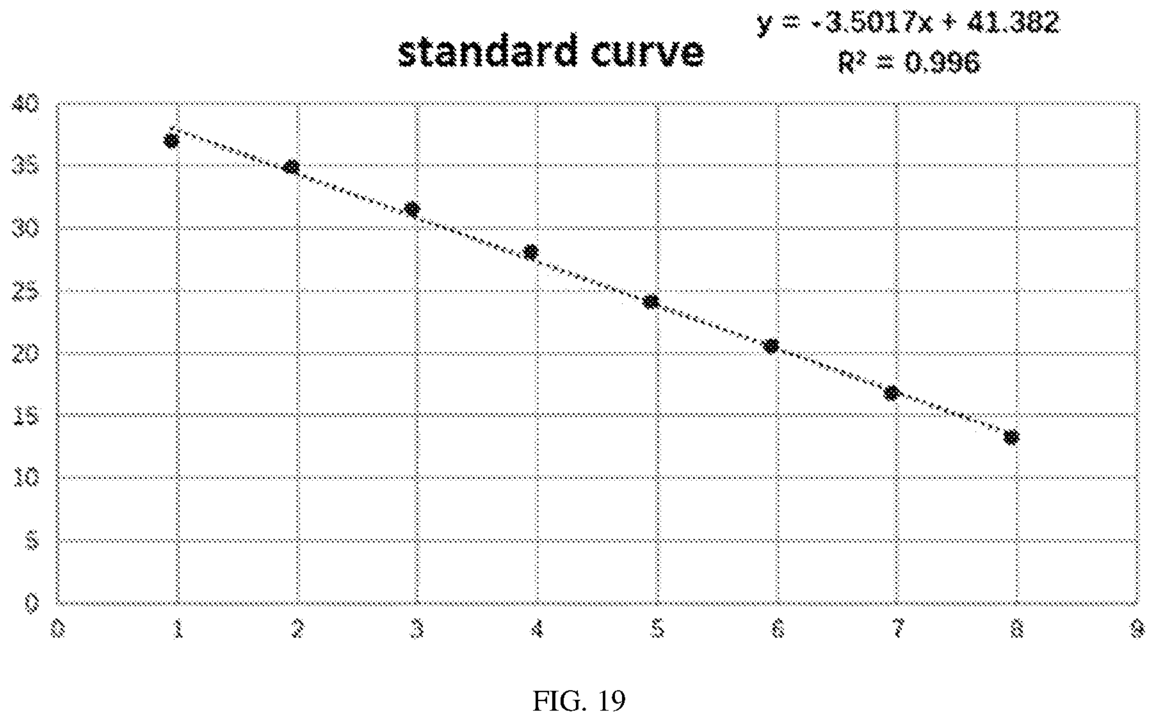
FIG. 19 is a quantitative standard curve obtained a PCR detection method.
Figure 20:
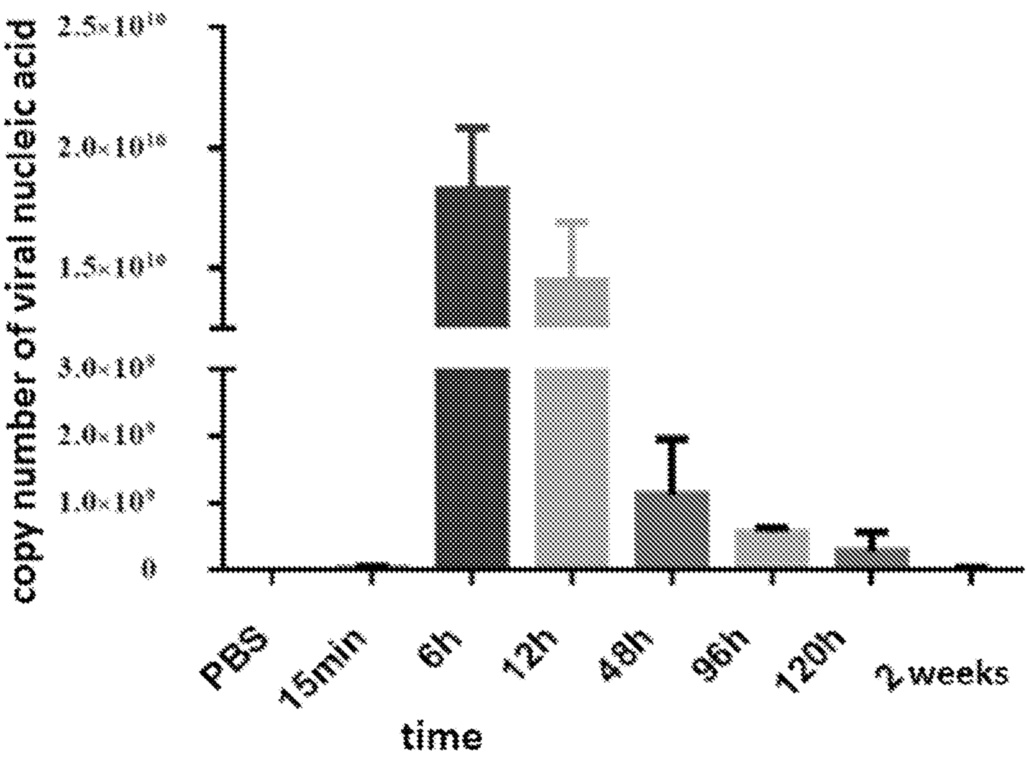
FIG. 20 is a schematic diagram of a nucleic acid copy number of JBS004 in the tumor at different time points in a LLC transplanted tumor model.
Figure 21:
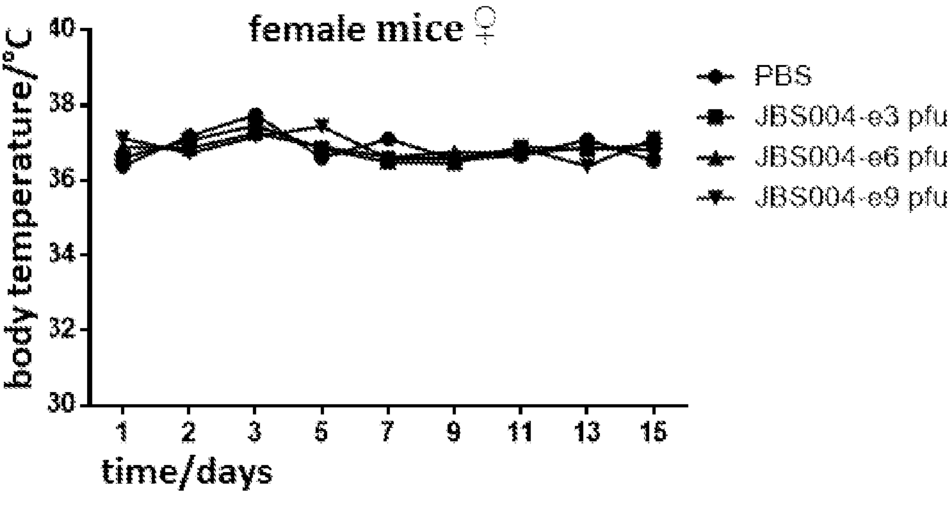
FIG. 21 is a schematic diagram showing an effect of JBS004 at different doses on body temperature of female mice at different time points.
Figure 22:
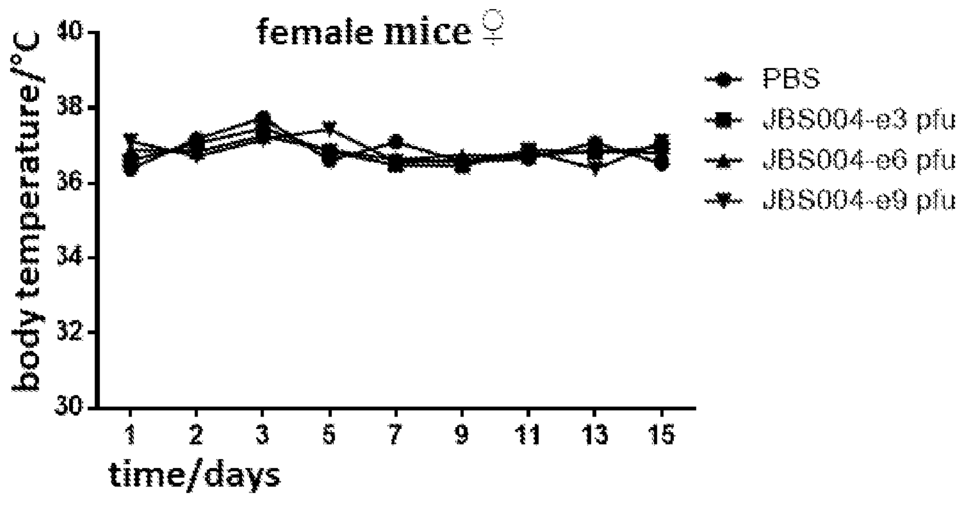
FIG. 22 is a schematic diagram showing an effect of JBS004 at different doses on body temperature of male mice at different time points.
Figure 23:
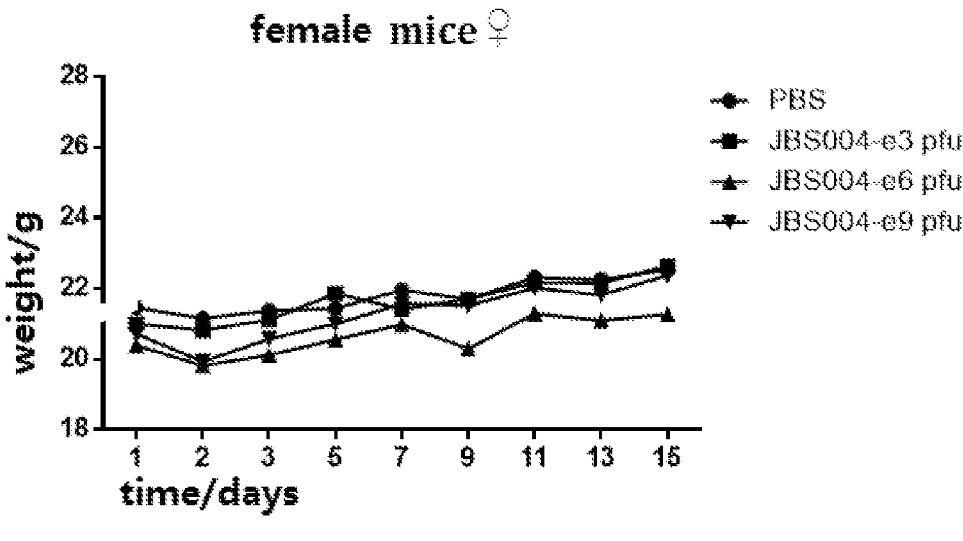
FIG. 23 is a schematic diagram showing an effect of JBS004 at different doses on weight of female mice at different time points.
Figure 24:
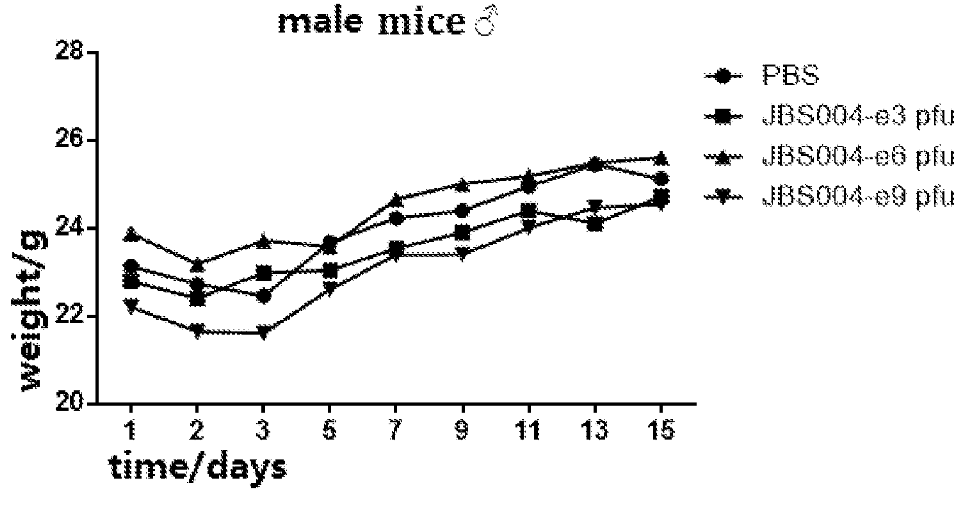
FIG. 24 is a schematic diagram showing an effect of JBS004 at different doses on weight of male mice at different time points.

1. The pharmacokinetics test. C57BL/6 mice were selected, and $2\times10^5$ of LLC cells were subcutaneously inoculated. After about 9 days of the inoculation, when the volume of the transplanted tumor was about 100 $mm^3$, a transplanted tumor model of LLC was established. JBS004 at $10^8$ pfu/mouse was intratumorally injected once, and the tumor tissues were sampled at 0 min (+15 min), 6 hours, 12 hours, 48 hours, 96 hours, 120 hours and 14 days respectively (repeated 3 copies), and the tumor tissues were broken with an automatic mill; total RNA of the tumor tissues were extracted by using Trizol, and finally a copy number of viral nucleic acids was analyzed with quantitative PCR (fluorescence probe method). Results were shown in FIG. 19 and FIG. 20.

The results indicated that an amount of the viruses in the tumors reached a peak at 6 hours of the infection, which was about 500 times more than the initial dose; at 48 hours of the infection, the amount of the viruses began to be lower than the initial dose; after 14 days, the copy number of viral nucleic acid was not detected.

Thus, JBS004 can be replicated in the tumors rapidly and efficiently; after 14 days, JBS004 was not detected, which proved that it will not accumulate in the body for a long time and will not cause potential subsequent damage, thus JBS004 had a good safety.

2. The acute toxicity test. 40 C57BL/6 mice with half male and half female were selected. The mice were divided into 3 administrated groups and a control group, and JBS004 solution was administered to the mice in the administration groups by single intramuscular injection, and the dose of each administration group respectively was: $10^3$ pfu/mouse, $10^6$ pfu/mouse and $10^9$ pfu/mouse. A menstruum was injected into the mice (single intramuscular injection of PBS) in the control group, and the volume of the administration was 100 μL. A day of the administration to the mice was defined as a first day of observing mice in this group. The mice were observed for 14 days after the administration to the animals and dissecting on 15th day after the administration.

During the experiment, the body temperature and the weight of the mice were recorded every 2 days. Results were shown in FIGS. 21-24. Before the administration and after the administration of 30 min, 1 h, 2 h, 4 h and 10 h, the mice were carefully observed at a side of a cage, and the mice were further carefully observed at the side of the cage at least once a day in subsequent experiments. At the end of the experiment, a peripheral blood of the mice was taken for hematology and blood biochemistry detection (blood glucose, creatinine, urea nitrogen, blood urea nitrogen/creatinine, phosphorus ion, calcium ion, total protein, albumin, globulin and etc.), and main organs, including heart, liver, spleen, lung, kidney, brain and testicle/ovary were collected during autopsy for weighing tissues, and calculating an organ coefficient.

Due to a length limitation, test results of indexes related to the hematology and the blood biochemistry were not listed all here. The test results indicated that there was no abnormal death of the mice and no clinical symptoms related to JBS004. Injection of JBS004 at different doses had no significant effect on a weight of an organ of the mice and the indexes related to the hematology and the blood biochemical of the mice. Under conditions of this experimental, a maximum tolerable dose (MTD) was at least $10^9$ pfu/mouse. Therefore, the above optimal dose ($10^8$ pfu/animal) was within the safe dose.

Example 4: Treatment Effects of the Oncolytic Virus Vaccine in Combination with PD-1 Antibody (PD1 Antibody) on the Non-Small Cell Lung Cancer C57BL/6 mice aged 6-8 weeks and weighed about 18 g were selected, and $2\times10^5$ non-small cell lung cancer LLC- NY-ESO-1 cells were inoculated subcutaneously, and the mice were treated when the volume of the transplanted tumor was about 100 $mm^3$. Treatment conditions of all of the groups were shown in Table 3, which included the control group (injected PBS), PD-1 antibody group, JBS004 group, JBS004 in combination with PD-1 antibody group, JBS005 group, JBS005 in combination with PD-1 antibody group, JBS006 group, JBS006 in combination with PD-1 antibody group, JBS007 group, JBS007 in combination with PD-1 antibody group, JBS011 group, JBS011 in combination with PD-1 antibody group, JBS012 group, JBS012 in combination with PD-1 antibody group, JBS013 group, JBS013 in combination with PD-1 antibody group, JBS014 group, JBS014 in combination with PD-1 antibody group, and 8 mice in each of the groups. The heavy chain variable region sequence of PD-1 antibody was shown in SEQ ID NO: 12, and the light chain variable region sequence was shown in SEQ ID NO: 13. JBS004 was injected intratumorally once every 2 days for 3 times in total at the single dose of $10^8$ pfu/mouse; the PD-1 antibody was injected intratumorally once every 2 days for 3 times in total at the single dose of 5 mg/kg, and an administration time was the same with JBS004.

TABLE 3 treatment conditions of each of the groups

| Groups | InjectedPD-1 Antibody or Not | Other |
|---|---|---|
| Control group | No | Equivalent PBS |
| PD-1 antibody group | Yes | / |
| JBS004 group | No | / |
| JBS004+PD-1 antibody group | Yes | / |
| JBS005 group | No | / |
| JBS005+PD-1 antibody group | Yes | / |
| JBS006 group | No | / |
| JBS006+PD-1 antibody group | Yes | / |
| JBS007 group | No | / |
| JBS007+PD-1 antibody group | Yes | / |
| JBS011 group | No | / |
| JBS011+PD-1 antibody group | Yes | / |
| JBS012 group | No | / |
| JBS012+PD-1 antibody group | Yes | / |
| JBS013 group | No | / |
| JBS013+PD-1 antibody group | Yes | / |
| JBS014 group | No | / |
| JBS014+PD-1 antibody group | Yes | / |

Figure 27:
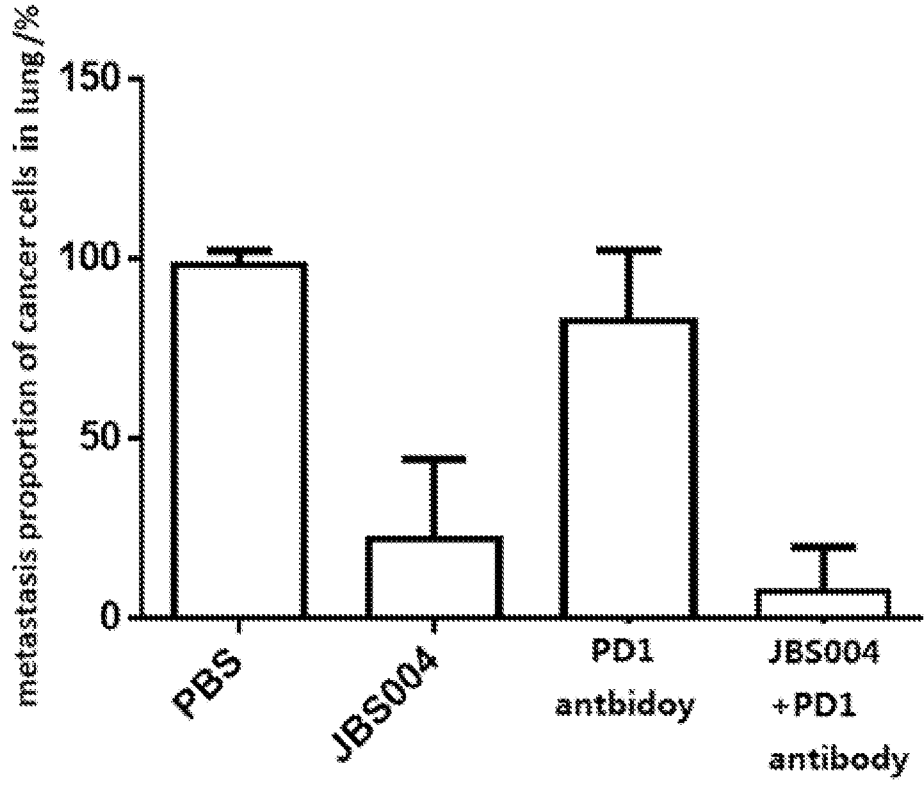
FIG. 27 is a schematic diagram showing an effect of treating with JBS004 separately or in combination with the PD-1 antibody on a metastasis of lung cancer cells.

From the beginning of the administration to the end of the experiment, the volume of the transplanted tumor was recorded every 2 days. At the end of the experiment, the mice were autopsied, and the lungs were taken and placed under a fluorescence microscope to take fluorescence pictures of the lungs. The change of the volume of the transplanted tumor in each of the groups was shown in FIG. 25 and FIG. 26. The metastasis of the lung cancer cell in each of the groups was shown in FIG. 27.

Figure 25:
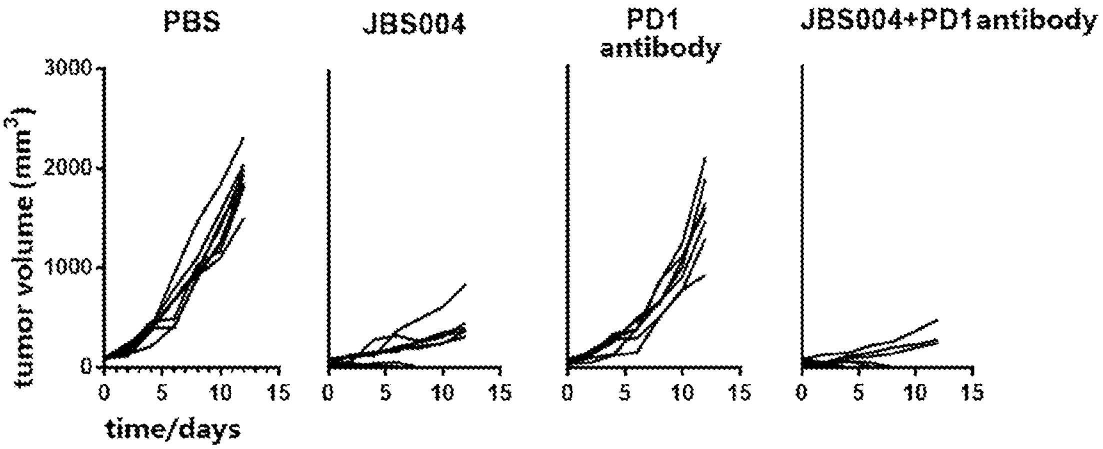
FIG. 25 is a schematic diagram showing an effect on a volume of lung cancer (transplanted tumor) treated with JBS004 separately or in combination with PD-1 antibody.
Figure 26A:
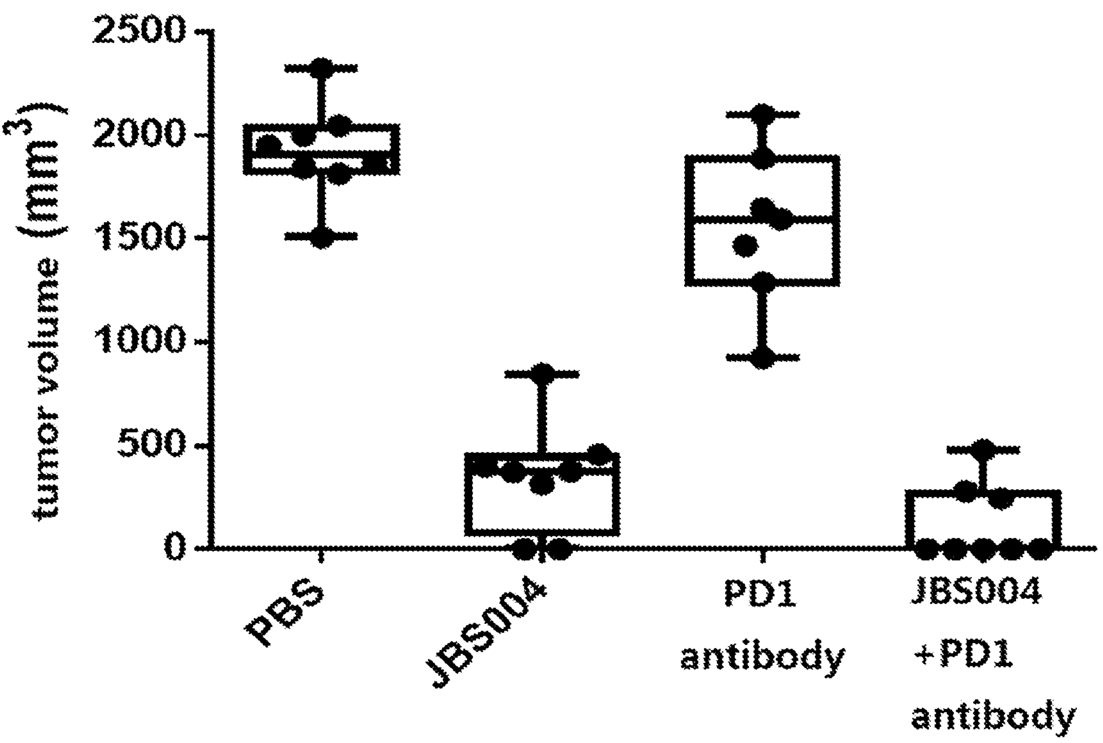
FIGS. 26A-26H are schematic diagrams of the volume of lung cancer (transplanted tumor) treated with the attenuated oncolytic virus strain/oncolytic virus vaccine described in the present application separately or in combination with PD-1 antibody at the end of the experiment.
Figure 26B:
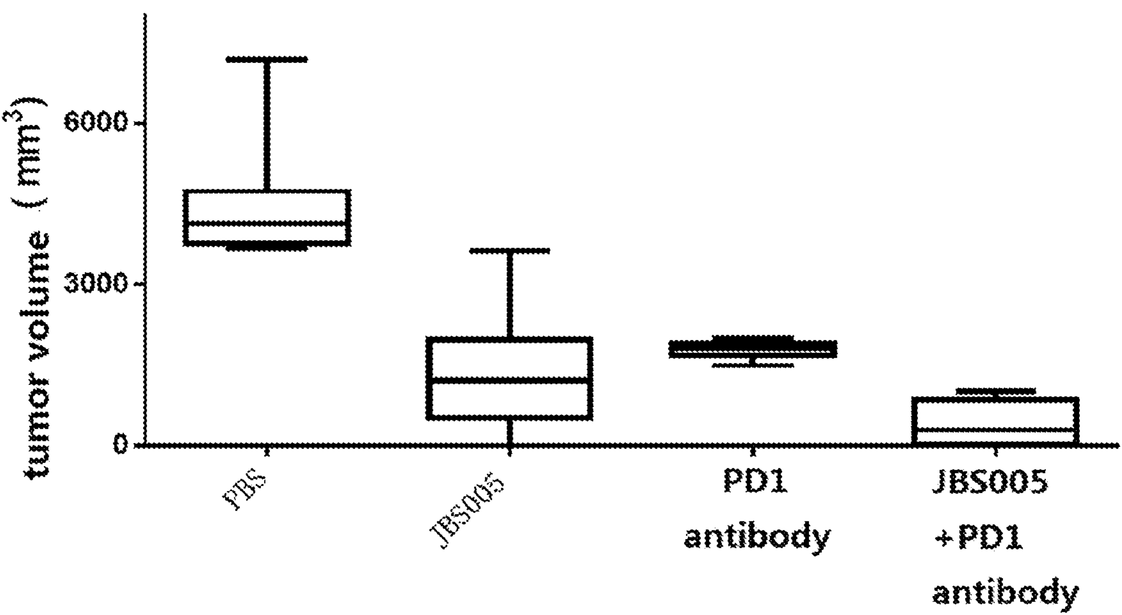
Figure 26C:
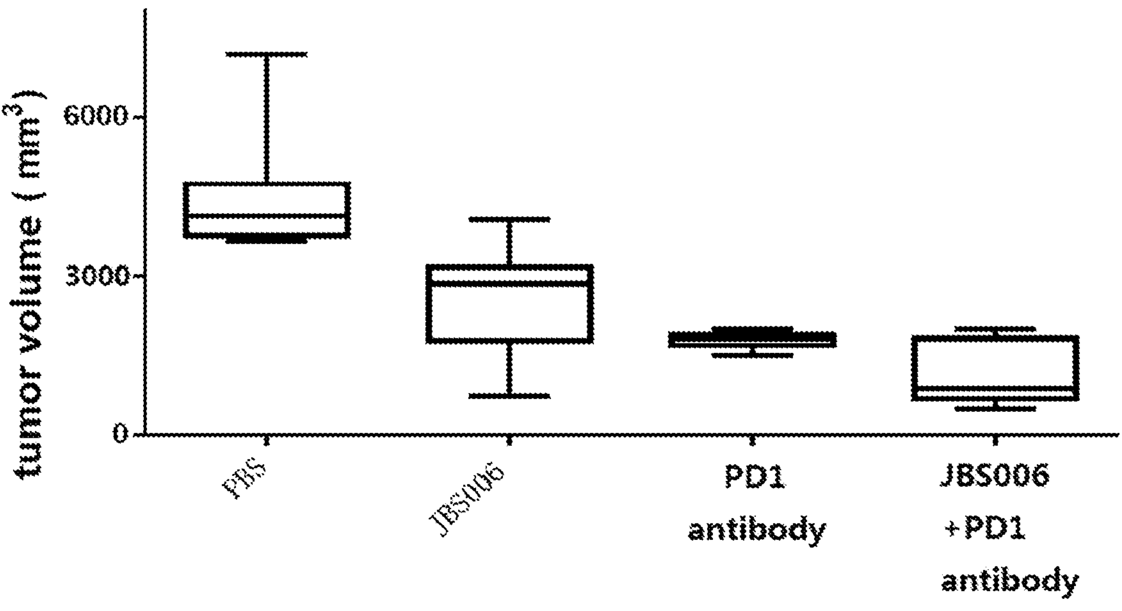
Figure 26D:
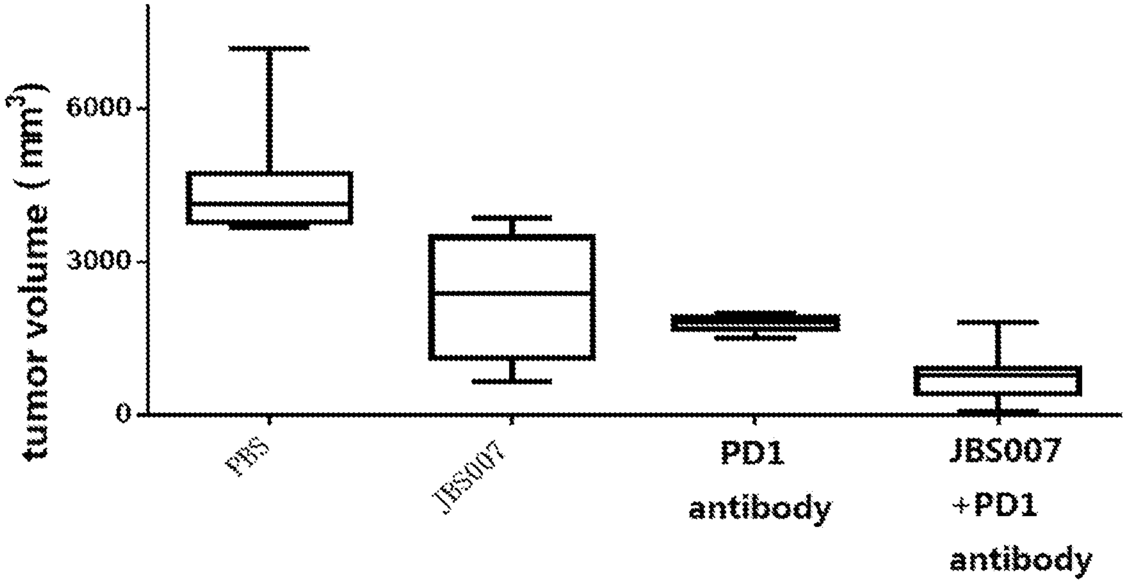
Figure 26E:
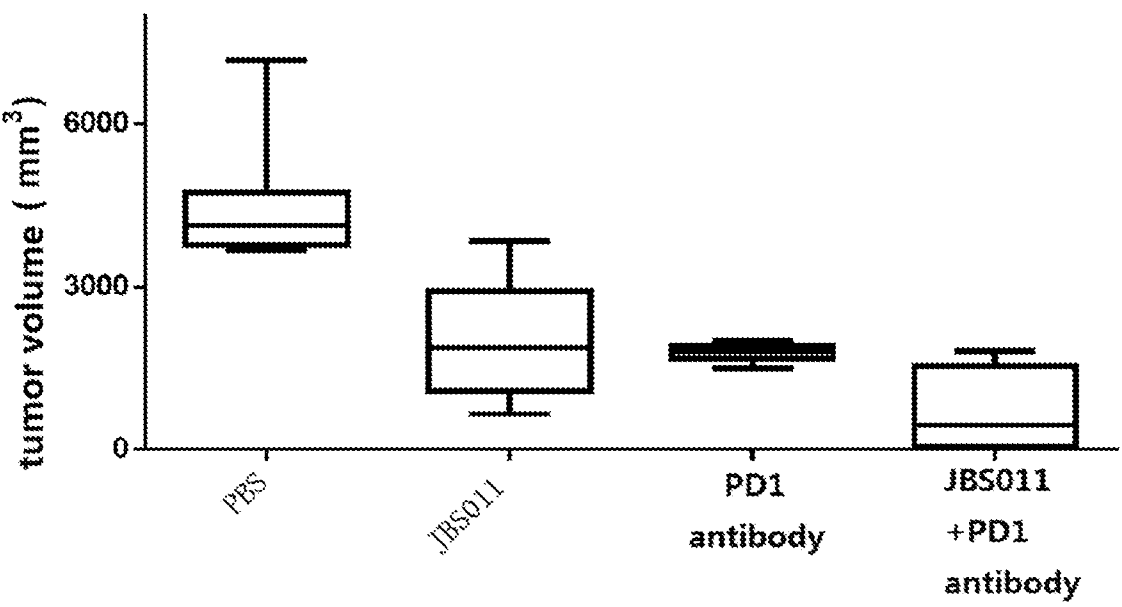
Figure 26F:
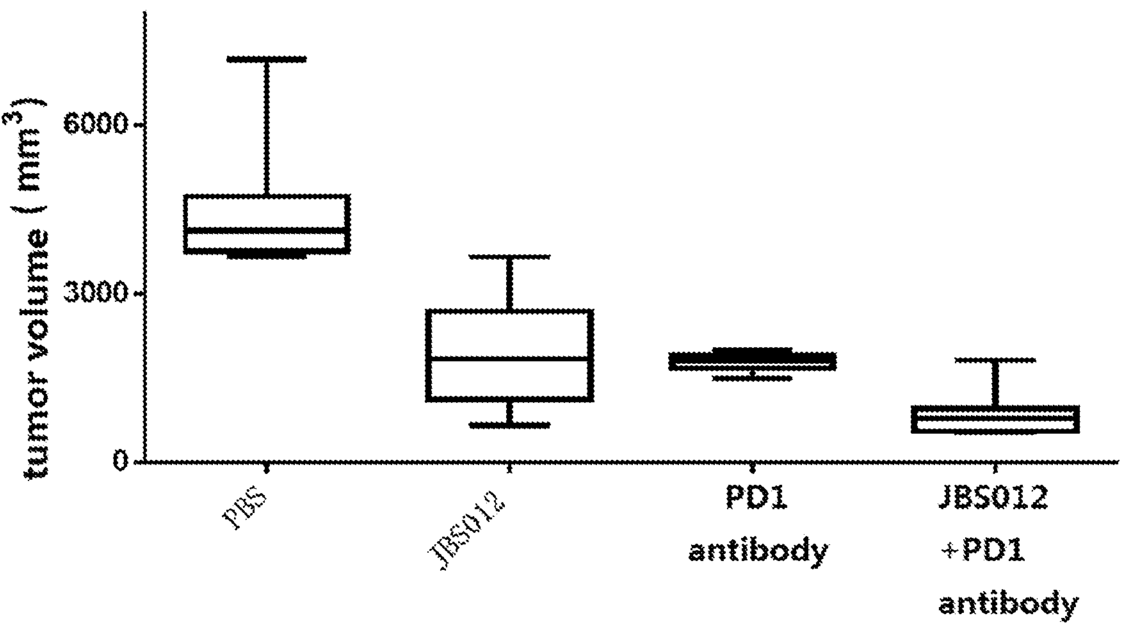
Figure 26G:
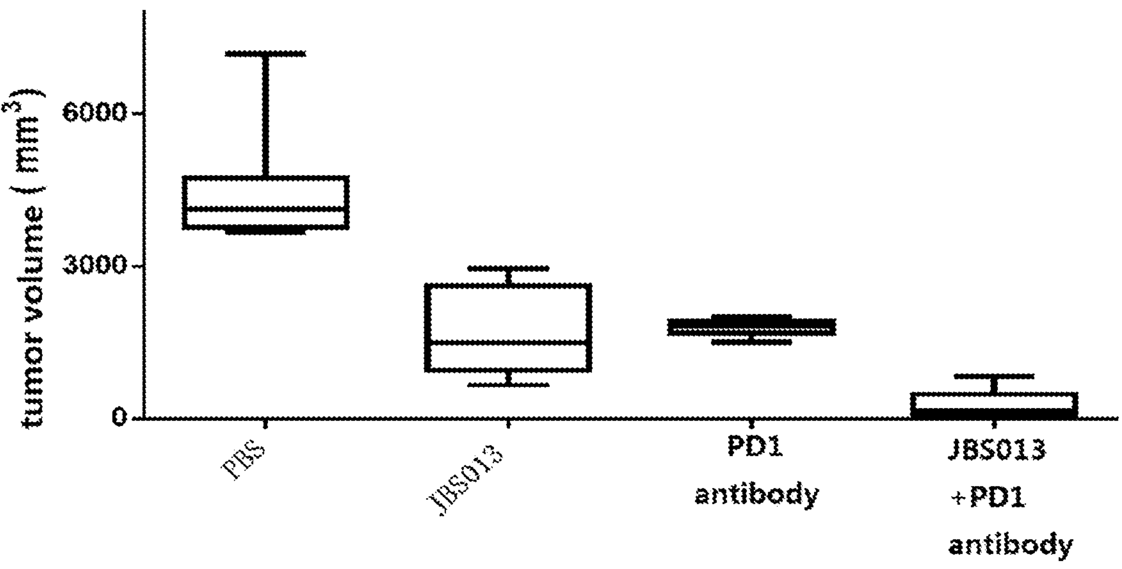
Figure 26H:
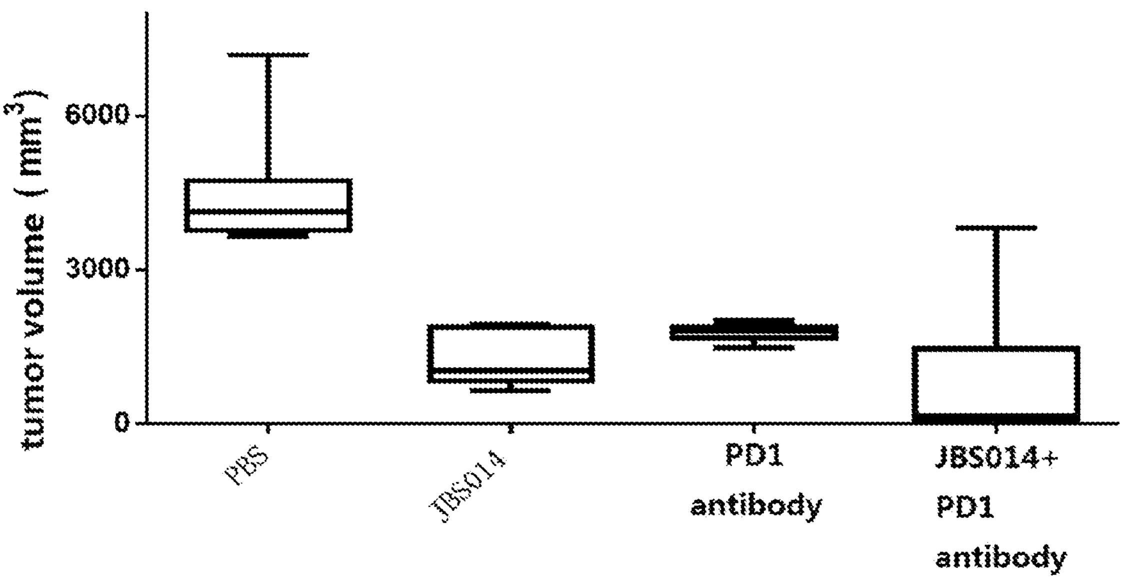

It can be seen from FIG. 25 and FIG. 26 that the tumor growth trend of the PBS group proved that a transplantation tumor model of lung cancer was successfully established. An inhibition effect of the oncolytic virus vaccine in combination with the PD-1 antibody on the tumor in each of the groups was better than that of the separate administration. Growth of the transplanted tumor was affected by separately intraperitoneal injection of the PD-1 antibody, but no transplanted tumor of the mice was completely cured. However, the volume of the transplanted tumor was controlled to some extent in the mice in JBS004 group and JBS004+PD1 antibody combined treatment group. In which, 2 mice in JBS004 group were completely cured, accounting for 25%; and 5 mice in JBS004+PD1 antibody group were completely cured, accounting for 62.5%. It can be seen from FIG. 27 that both JBS004 group and JBS004+PD1 antibody group can inhibit the metastasis of the cancer cells of the lung cancer transplanted tumor to some extent, and after JBS004 was administrated in combination with the PD1 antibody, an inhibition effect on the metastasis of the cancer cell in JBS004+PD1 antibody group was significantly better than that in other groups.

Example 5: When the Oncolytic Virus Vaccine was Administrated in Combination with the PD-1 Antibody, Effects of Providing the PD-1 Antibody at Different Doses The transplantation tumor model of lung cancer (LLC-NY-ESO-1, mouse) was established according to the method in Example 4, and the mice were treated when the volume of the transplanted tumor was about 100 $mm^3$. The control group (injected PBS), JBS004 group (intratumorally injected JBS004 only) and JBS004+PD-1 antibody dose group were set; in JBS004+PD-1 antibody dose group, PD-1 antibody at dose levels of 1 mg/kg, 5 mg/kg and 10 mg/kg was administered by intraperitoneal injection, and 8 mice in each of the groups. In all of the above groups, JBS004 was injected intratumorally at the single dose of $10^8$ pfu/mouse; the administration was performed once every two days for 3 times in total, and the administration time of JBS004 and the PD-1 antibody was the same.

Figure 28:
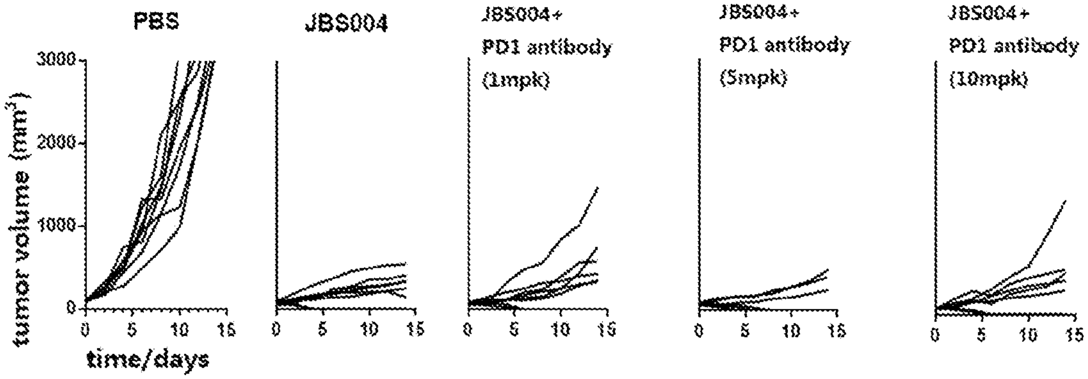
FIG. 28 is a schematic diagram showing an effect of treating with JBS004 in combination with the PD-1 antibody at different doses on a volume of lung cancer (transplanted tumor)
Figure 29:
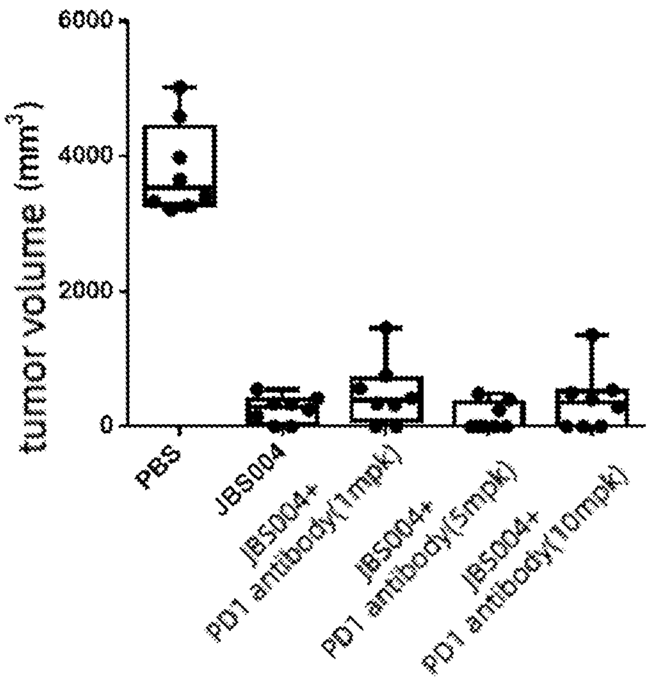
FIG. 29 is a schematic diagram of the volume of lung cancer (transplanted tumor) treated with JBS004 in combination with the PD-1 antibody at different doses at the end of the experiment.
Figure 30:
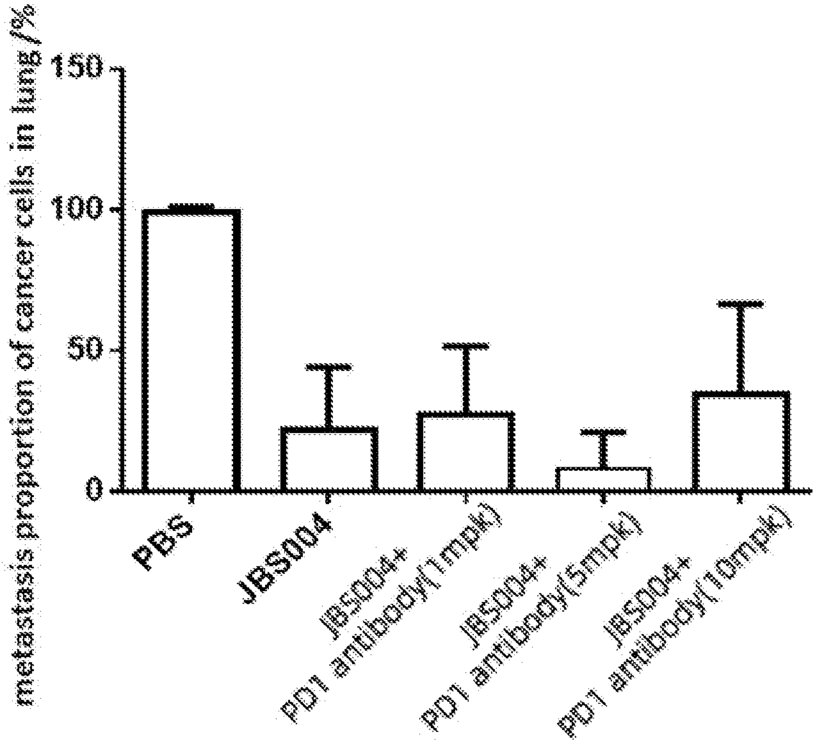
FIG. 30 is a schematic diagram showing an effect of treating with JBS004 in combination with the PD-1 antibody at different doses on a metastasis of lung cancer cells.

The change of the tumor volume in each of the groups was shown in FIG. 28 and FIG. 29; the metastasis of the cancer cell in each of the groups was shown in FIG. 30. It can be seen from the figures that a treatment effectiveness of each of the other combined treatment groups was improved to some extent except the JBS004+PD-1 antibody dose group with 1 mg/kg. The cure rate of JBS004 was 25%; when the PD-1 antibody was 5 mg/kg, the cure rate was 62.5%, and the inhibition effect on the metastasis of the cancer cells was the most obvious; when the PD-1 antibody was 10 mg/kg, the cure rate was 37.5%, and the inhibition effect on the metastasis of the cancer cells was weaker than that in the group administrating JBS004 separately and the group with the PD-1 antibody dose of 1 mg/kg.

In summary, when administrated in combination with JBS004, an optimal dose of the PD-1 antibody was 5 mg/kg.

Example 6: When the Oncolytic Virus Vaccine was Administrated in Combination with the PD-1 Antibody, Effects of Different Administration Routes of JBS004

The administration routes of JBS004 included nasal drip, intratumoral injection, intravenous injection and intraperitoneal injection; considering a convenience of clinical administration, this example only shown the intratumoral injection and the intravenous injection. The transplantation tumor model of lung cancer (LLC-NY-ESO-1, mouse) was established according to the method in Example 4, and the mice were treated when the volume of the transplanted tumor was about 100 $mm^3$. The control group (injected PBS), separately intratumorally injected JBS004 group (IT), separately intravenously injected JBS004 group (IV), intratumorally injected JBS004 (IT) in combination with PD-1 antibody group, intravenously injected JBS004 (IV) in combination with PD-1 antibody group were set, and 8 mice in each of the groups. In which, intravenously injected JBS004 at the dose of $10^9$ pfu/mouse, and intratumorally injected JBS004 at the dose of $10^8$ pfu/mouse; the PD-1 antibody was administrated by the intraperitoneal injection at the single dose of 5 mg/kg. The administration was performed once every 2 days for 3 times in total, and the administration time of JBS004 and the PD-1 antibody was the same. The dose of intravenous injection was greater than the dose of intratumoral injection, which was because there was a certain loss of the medicine in the body after the intravenous injection and before the medicines arriving at the tumors; in order to ensure that the medicine amount when arriving at the tumors was equivalent to that of the intratumoral injection group, the dose of the intravenous injection was increased.

Figure 31:
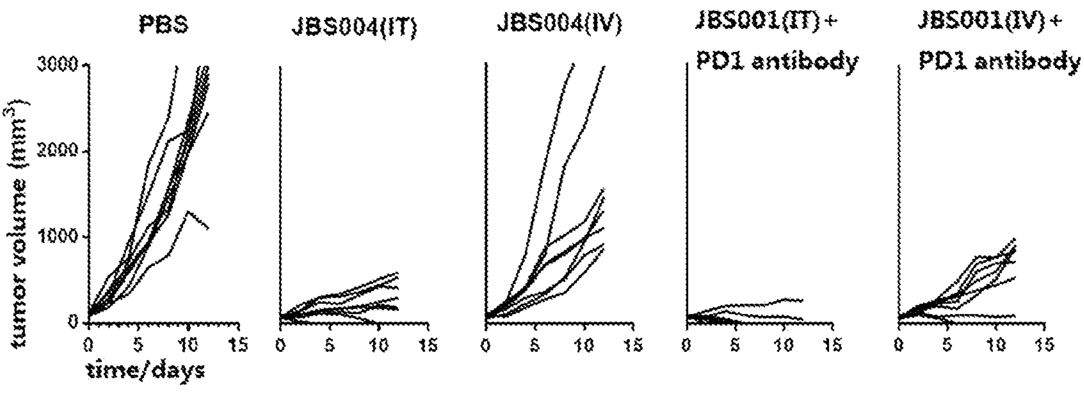
FIG. 31 is a schematic diagram showing an effect of treating with JBS004 in combination with the PD-1 antibody by different administration routes on a volume of lung cancer cells.
Figure 32:
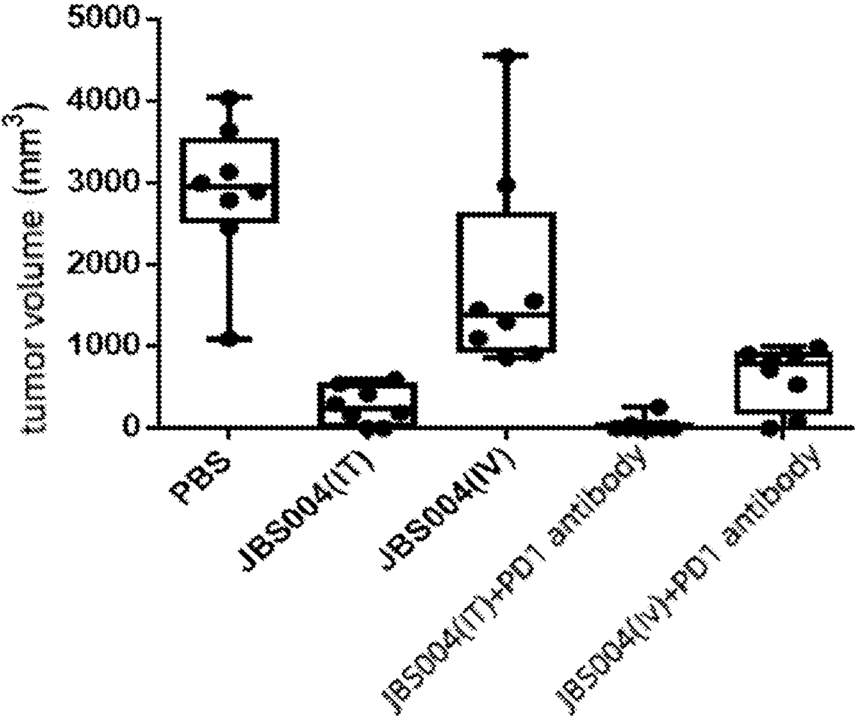
FIG. 32 is a schematic diagram of the volume of lung cancer (transplanted tumor) treated with JBS004 in combination with the PD-1 antibody by different administration routes at the end of the experiment.
Figure 33:
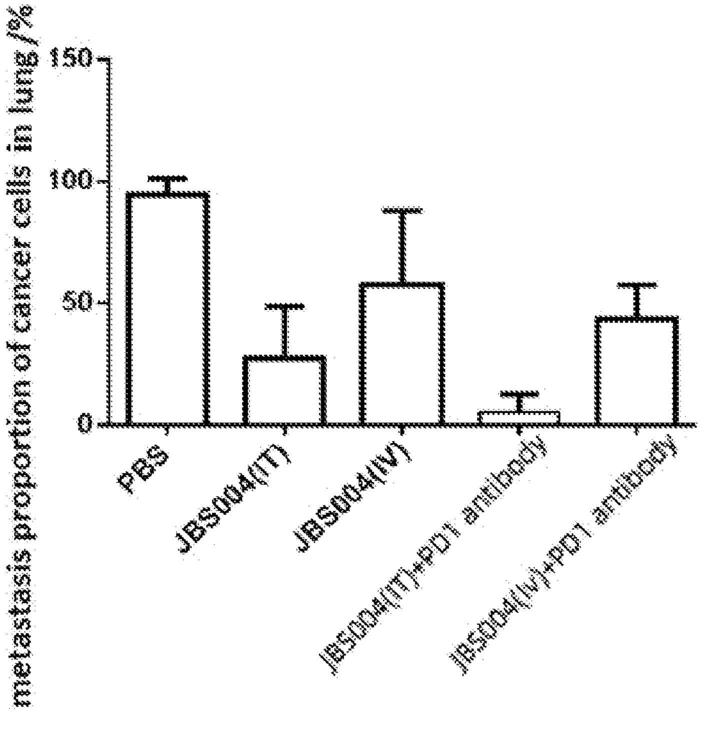
FIG. 33 is a schematic diagram showing an effect of treating with JBS004 in combination with the PD-1 antibody by different administration routes on a metastasis of lung cancer cells.

The change of the tumor volume in each of the groups was shown in FIG. 31 and FIG. 32; the metastasis of the cancer cells was shown in FIG. 33. It can be seen from the figures that the intratumoral injection was significantly better than the intravenous injection. The cure rate was 62.5% after the treatment by intratumorally injected JBS004 in combination with the PD-1 antibody; under the same conditions, the cure rate when intravenously injected JBS004 was only 12.5%.

Example 7: When the Oncolytic Virus Vaccine was Administrated in Combination with the PD-1 Antibody, Effects of Different First Administration Order In theory, when JBS004 plays a role of oncolysis, it kills the tumors mainly by T cells recruitment and infiltration to a local of the tumors. After T cells arriving at the local of the tumors, they needed to fight against the cytokines in a micro-environment in the tumors, thus weakening an oncolysis effect and killing ability to some extent. If the PD-1 antibody can be injected in advance, it may effectively block an immune examination of the local of the tumors, thus enhancing the oncolysis effect of JBS004. Preliminary tests and theoretical analysis show that the first administration order has a great effect on the treatment effect, but a subsequent administration order has a low correlation with the treatment effect. Thus, this example only shown a relationship between the first administration order and the treatment effect. Reasons for a high correlation between the first administration order and the treatment effect may be: (1) at the first administration, the tumor volume is relatively small, and the micro-environment in the tumors is easier to be broken; (2) there are certain amounts of the PD-1 antibody in the body at the sub sequent administration.

The transplantation tumor model of lung cancer (LLC-NY-ESO-1, mouse) was established according to the method in Example 4, and the mice were treated when the volume of the transplanted tumor was about 100 $mm^3$ 0.8 mice were set in each of the groups, and intratumorally injected JBS004 at the single dose of $10^8$ pfu/mouse; intraperitoneally injected the PD-1 antibody at the single dose of 5 mg/kg; the administration was performed every 2 days for 3 times in total. The PBS group was set in which the mice were intraperitoneally injected 200 μL of PBS, and intratumorally injected 50 μL of PBS at the same time; group 1 was set in which the mice were intraperitoneally injected the PD-1 antibody, and intratumorally injected JBS004 at the same time; group 2 was set in which the mice were intraperitoneally injected the PD-1 antibody first, and intratumorally injected JBS004 after 6 hours; group 3 was set in which the mice were intratumorally injected JBS004 first, and intraperitoneally injected the PD-1 antibody after 6 hours.

Figure 34:
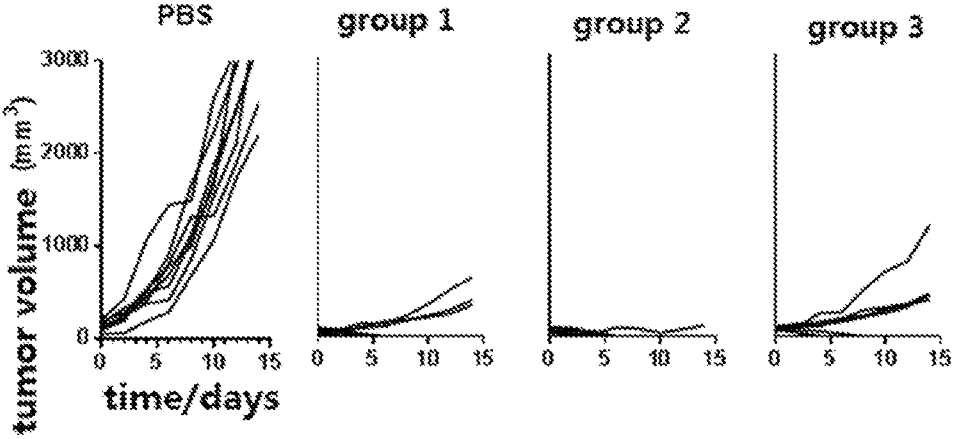
FIG. 34 is a schematic diagram showing an effect of treating with JBS004 in combination with the PD-1 antibody by different administration orders on a volume of lung cancer (transplanted tumor)
Figure 35:
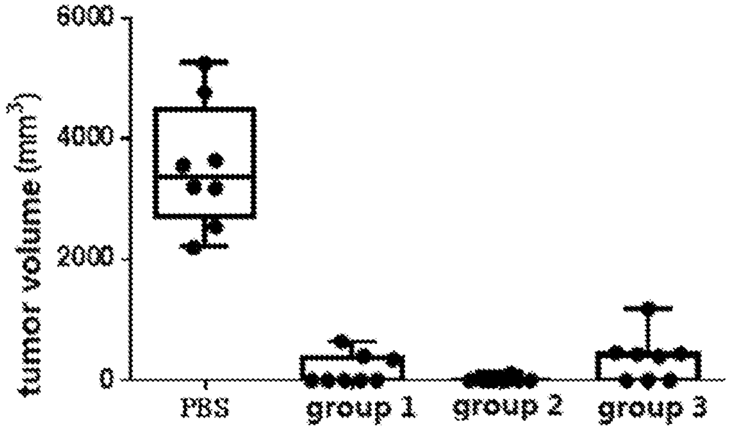
FIG. 35 is a schematic diagram of the volume of lung cancer (transplanted tumor) treated with JBS004 in combination with the PD-1 antibody by different administration orders at the end of the experiment.
Figure 36:
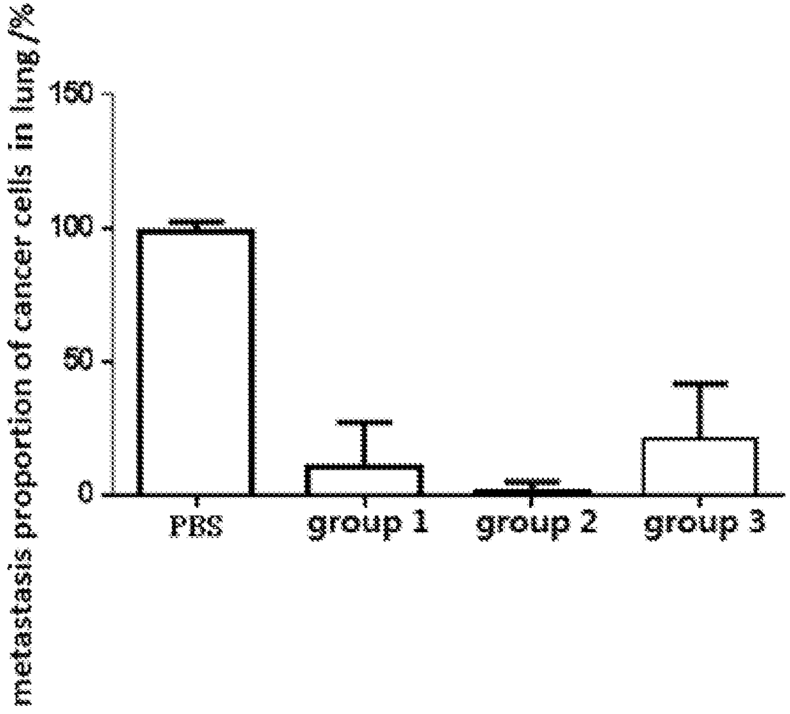
FIG. 36 is a schematic diagram showing an effect of treating with JBS004 in combination with the PD-1 antibody by different administration orders on a metastasis of lung cancer cells.

The change of the tumor volume in each of the groups was shown in FIG. 34 and FIG. 35; the metastasis of the cancer cells was shown in FIG. 36. The cure rate was 62.5% when administrated at the same time; the cure rate dropped to 37.5% in the group of injected JBS004 first; the cure rate reached 87.5% in the group of injected the PD-1 antibody first, and the treatment effectiveness was significantly improved.

In summary, when administrated the PD-1 antibody first and then administrated the JBS004 for a combined treatment, the treatment effect was the best. Namely: when administrated JBS004 in combination with the PD-1 antibody, the PD-1 antibody is released (plays a role) in the body before JBS004, which is more conducive to improving the treatment effect. In a practical application, in order to realize a purpose of the PD-1 antibody released first or arriving at the tumors to play a role, the medicine can be administered sequentially, or by a pharmaceutical mean. When administrated sequentially, the medicine can be administrated by intravenous injection, intratumoral injection, intraperitoneal injection, subcutaneous injection and etc. When administrated by the pharmaceutical mean, JBS004 and PD-1 can be prepared to a whole medicine, and a release order and a release time of JBS004 and PD-1 can be controlled by capsuling coating and other means during a preparation process.

Example 8: Effects of JBS004 in Combination with the PD-1 Antibody on the Treatment of Other Tumors (Cancers)

In this example, 8 mice were set in each of the groups, and intratumorally injected JBS004 at the single dose of $10^8$ pfu/mouse; intraperitoneally injected the PD-1 antibody at the single dose of 5 mg/kg; the administration was performed once every 2 days for 3 times in total. The administration order was: administrated the PD-1 antibody first and administrated JBS004 after 6 hours.

1. The effects of JBS004 in combination with the PD-1 antibody in the treatment of the breast cancer (transplanted tumor).

BALB/c mice were in situ inoculated with $5\times10^5$ of 4 T1-NY-ESO-1 cells (breast cancer cells), the mice were treated when the volume of the transplanted tumor was about 100 $mm^3$. The PBS group, separately injected JBS004 group, separately injected the PD-1 antibody group, and JBS004 in combination with the PD-1 antibody group were set.

Figure 37:
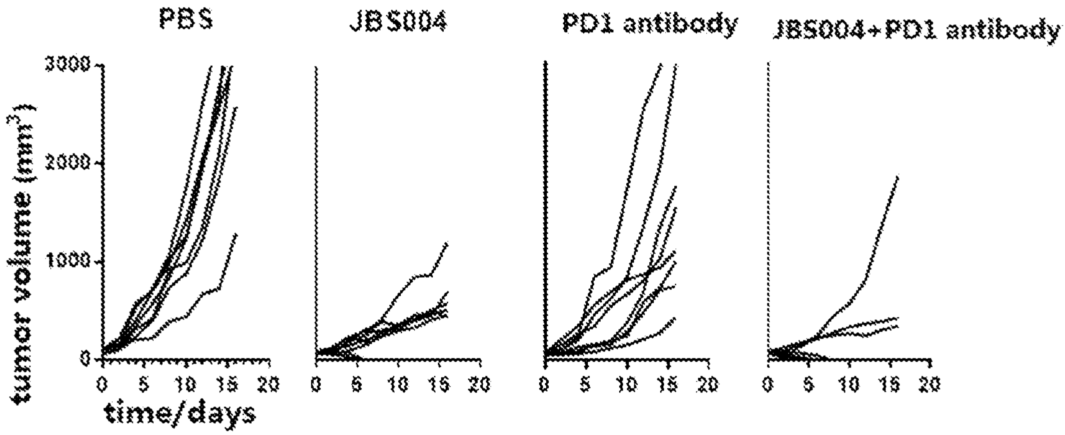
FIG. 37 is a schematic diagram shows an effect of treating with JBS004 in combination with the PD-1 antibody on a volume of breast cancer (transplanted tumor)
Figure 38:
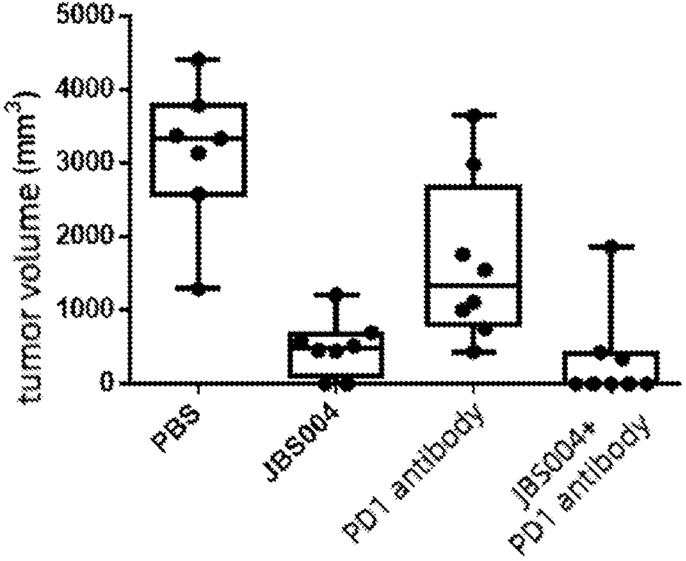
FIG. 38 is a schematic diagram of the volume of breast cancer (transplanted tumor) treated with JBS004 in combination with the PD-1 antibody at the end of the experiment.

The change of the tumor volume in each of the groups was shown in FIG. 37 and FIG. 38. The cure rate of JBS004 in combination with the PD-1 antibody group was 62.5%, and the treatment effectiveness was 100%, and the effect was significantly better than other groups.

2. The effects of JBS004 in combination with the PD-1 antibody in the treatment of a colon cancer (transplant tumor, large tumor). According to current clinical tests, known medicines for treating cancers are ineffective to the large tumors exceeding a certain volume.

C57BL/6 mice were subcutaneously inoculated with MC38-NY-ESO-1 cells (colon cancer cells), the mice were treated when the volume of the transplanted tumor was between 200 $mm^3$ and 300 $mm^3$. The PBS group, separately injected JBS004 group, separately injected the PD-1 antibody group, and JBS004 in combination with the PD-1 antibody group were set.

Figure 39:
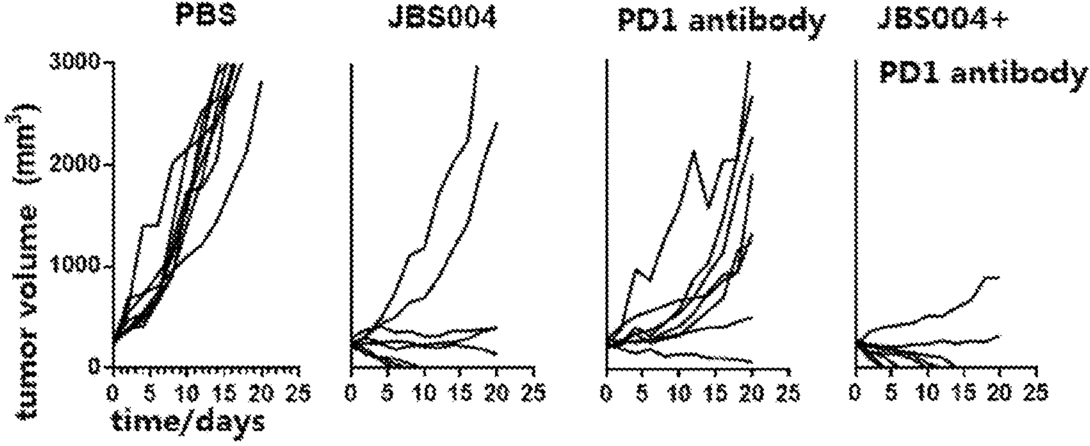
FIG. 39 is a schematic diagram showing an effect of treating with JBS004 in combination with the PD-1 antibody on a volume of colon cancer (transplant tumor, large tumor)
Figure 40:
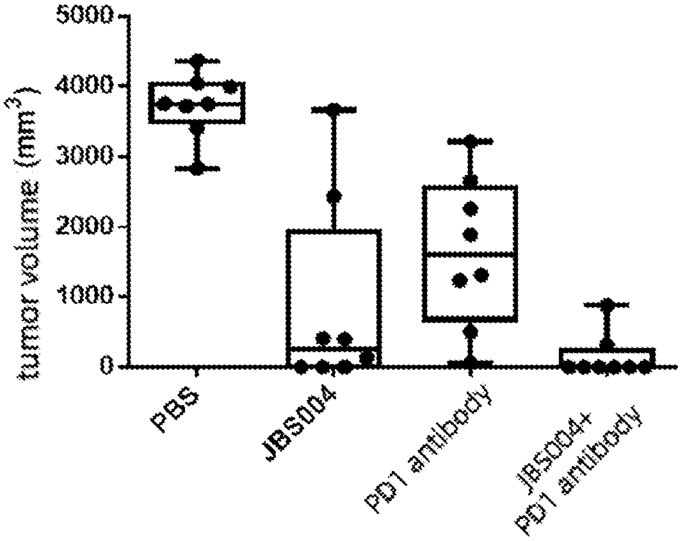
FIG. 40 is a schematic diagram of the volume of colon cancer (transplant tumor, large tumor) treated with JBS004 in combination with the PD-1 antibody at the end of the experiment.

The change of the tumor volume in each of the groups was shown in FIG. 39 and FIG. 40. It can be seen that when separately administrated JBS004, the colon cancer large tumor can be cured to some extent. At the same time, the inventor was surprised to find that under conditions of this model, the PD-1 antibody also had a certain expected effect on the large tumors. The cure rate of the combined treatment group reached 75%, which was significantly better than the separately administration of the both.

The foregoing detailed description is provided in the form of explanations and examples, and is not intended to limit the scope of the attached claims. At present, various changes in the embodiments listed in the present application are obvious to those skilled in the art, and fall into the scope of the claims and their equivalents.

What is claimed is:

1. A pharmaceutical composition, comprising an attenuated oncolytic virus strain and an immune checkpoint inhibitor, wherein the attenuated oncolytic virus strain is a vesicular stomatitis virus (VSV) MuddSummer subtype strain with an engineered matrix protein M, an engineering of the engineered matrix protein M comprises knocking out of leucine-encoding bases at position 111 of an amino acid sequence of a wild-type matrix protein M, and the amino acid sequence of the wild-type matrix protein M is shown as SEQ ID NO: 2;

wherein an amino acid sequence of the engineered matrix protein M of the attenuated oncolytic virus strain is any one selected from a group consisting of the following amino acid sequences: SEQ ID NO: 4, SEQ ID NO: 7, SEQ ID NO: 8, SEQ ID NO: 9, SEQ ID NO: 10, and SEQ ID NO: 11.

2. A pharmaceutical composition, comprising an oncolytic virus vaccine prepared by using the pharmaceutical composition according to claim 1, wherein the oncolytic virus vaccine is prepared by inserting an antigen into the attenuated oncolytic virus strain.

3. The pharmaceutical composition according to claim 2, wherein the antigen is a specific tumor antigen.

4. The pharmaceutical composition according to claim 2, wherein the antigen is any one selected from a group consisting of: NY-ESO-1, gp33, gp100, TX103, Mucin-1, WT-1, MART-1, MAGE A1, MAGE A3, MAGE A4, MAGE B2, PRAME, SURVIVIN, MART-1, col6A3, tyrosinase, T antigen, SLC45A2, VCX/Y, HPV, alpha fetoprotei, carcinoembryonic antigen, CA 125, Her2, dopachrome tautomerase, BAGE protein, GAGE protein, survivin, tyrosinase, SSX2, cyclin-A1, KIF20A, MUC5AC, Meloe, Lengsin, kallikrein4, IGF2B3 and glypican 3.

5. The pharmaceutical composition according to claim 1, wherein the immune checkpoint inhibitor is one selected from a group consisting of: anti-PD-1 antibody, anti-PD-L1 antibody, anti-CTLA4 antibody, anti-LAG-3 antibody, anti-TIM-3 antibody and anti-SIGLEC15 antibody.

6. The pharmaceutical composition according to claim 2, wherein the immune checkpoint inhibitor is released in a body before the oncolytic virus vaccine.

7. The pharmaceutical composition according to claim 1, wherein the pharmaceutical composition is configured to be used for resisting a tumor or treating a cancer.

8. The pharmaceutical composition according to claim 7, wherein the tumor or the cancer is one selected from a group consisting of: head and neck cancer, melanoma, soft tissue sarcoma, breast cancer, esophageal cancer, lung cancer, ovarian cancer, bladder cancer, liver cancer, cervical cancer, neuroblastoma, synovial sarcoma, and round cell liposarcoma.

* * * * *